(12) United States Patent
Chen et al.

(10) Patent No.: US 7,964,746 B2
(45) Date of Patent: Jun. 21, 2011

(54) COPPER PRECURSORS FOR CVD/ALD/DIGITAL CVD OF COPPER METAL FILMS

(75) Inventors: Tianniu Chen, Rocky Hill, CT (US); Chongying Xu, New Milford, CT (US); Thomas H. Baum, New Fairfield, CT (US); Bryan C. Hendrix, Danbury, CT (US); Jeffrey F. Roeder, Brookfield, CT (US); Juan E. Dominguez, Hillsboro, OR (US); Adrien R. Lavoie, Beaverton, OR (US); Harsono S. Simka, Saratoga, CA (US)

(73) Assignee: Advanced Technology Materials, Inc., Danbury, CT (US)

( * ) Notice: Subject to any disclaimer, the term of this patent is extended or adjusted under 35 U.S.C. 154(b) by 385 days.

(21) Appl. No.: 12/058,751

(22) Filed: Mar. 30, 2008

(65) Prior Publication Data

US 2008/0242880 A1    Oct. 2, 2008

Related U.S. Application Data

(60) Provisional application No. 60/908,998, filed on Mar. 30, 2007.

(51) Int. Cl.
*C07F 1/08*    (2006.01)
*C23C 18/40*    (2006.01)
(52) U.S. Cl. .......... 556/112; 556/8; 556/9; 549/3; 549/206; 548/402; 118/726; 106/1.26
(58) Field of Classification Search .......... 556/8, 9, 556/112; 118/726; 106/1.26; 549/3, 206; 548/402
See application file for complete search history.

(56) References Cited

U.S. PATENT DOCUMENTS

| | | | | |
|---|---|---|---|---|
| 4,927,670 A | * | 5/1990 | Erbil | 505/447 |
| 4,948,623 A | * | 8/1990 | Beach et al. | 427/586 |
| 6,086,779 A | | 7/2000 | Bishop et al. | |
| 6,269,979 B1 | | 8/2001 | Dumont | |
| 2004/0215030 A1 | | 10/2004 | Norman | |
| 2005/0283012 A1 | | 12/2005 | Xu et al. | |
| 2006/0141155 A1 | | 6/2006 | Gordon et al. | |

FOREIGN PATENT DOCUMENTS

SU    768457    * 10/1980

OTHER PUBLICATIONS

Macomber et al., Journal of American Chemical Society, vol. 105, No. 16, pp. 5325-5329 (1983).*

(Continued)

*Primary Examiner* — Porfirio Nazario Gonzalez
(74) *Attorney, Agent, or Firm* — Steven J. Hultquist; Hulquist IP; Margaret Chappuis

(57) ABSTRACT

Copper precursors useful for depositing copper or copper-containing films on substrates, e.g., microelectronic device substrates or other surfaces. The precursors includes copper compounds of various classes, including copper borohydrides, copper compounds with cyclopentadienyl-type ligands, copper compounds with cyclopentadienyl-type and isocyanide ligands, and stabilized copper hydrides. The precursors can be utilized in solid or liquid forms that are volatilized to form precursor vapor for contacting with the substrate, to form deposited copper by techniques such as chemical vapor deposition (CVD), atomic layer deposition (ALD) or rapid vapor deposition (digital CVD).

14 Claims, 5 Drawing Sheets

OTHER PUBLICATIONS

Anderson et al., Organometallics, vol. 17, No. 22, pp. 4917-4920 (1998).*

Artaud-Gillet et al., Journal of Crystal Growth, vol. 248, pp. 163-168 (2003).*

Ren et al., Journal of Organometallic chemistry, vol. 691, pp. 4109-4113 (available in the Web Jun. 21, 2006).*

Li, Wentao, et al., "Additives for stabilizing LiPF6-based electrolyes against thermal decomposition", "J. Electrochem. Soc.", 2005, pp. A1361-A1365, vol. 152, No. 7.

Oakley, Sarah H., et al., "Structural consequences of the prohibition of hydrogen bonding in copper-guanidine systems", "Inorg. Chem.", 2004, pp. 5168-5172, vol. 43, No. 16.

* cited by examiner

COPPER PRECURSORS FOR CVD/ALD/DIGITAL CVD OF COPPER METAL FILMS

CROSS-REFERENCE TO RELATED APPLICATION

The benefit of U.S. Provisional Patent Application 60/908, 998 filed Mar. 30, 2007 in the names of Tianniu Chen, et al. for "COPPER PRECURSORS FOR CVD/ALD/DIGITAL CVD OF COPPER METAL FILMS" is hereby claimed under the provisions of 35 USC 119. The disclosure of said U.S. Provisional Patent Application 60/908,998 is hereby incorporated herein by reference, in its entirety, for all purposes.

FIELD OF THE INVENTION

The present invention relates to copper precursors useful for deposition of copper, e.g., on a microelectronic device substrate, as well as to corresponding deposition methods utilizing such precursors, and to microelectronic device structures and products formed by use of such copper precursors and deposition methods.

DESCRIPTION OF THE RELATED ART

As a result of its low resistivity, low contact resistance, and ability to enhance device performance through the reduction of RC time delays, copper has emerged as a preferred metal for metallization of very large scale integrated (VLSI) devices. Copper metallization has been adopted by many microelectronic device manufacturers for production of microelectronic chips, thin-film recording heads and packaging components.

Two primary factors—the lower resistivity and the increased electromigration resistance that copper offers relative to aluminum have rapidly accelerated the conversion from aluminum to copper interconnects in IC chips manufacturing. This transition has resulted in the introduction of many new processes and materials, but at the same time has posed significant challenges to the microelectronics manufacturing industry. The deposition of the copper thin films at the lower interconnect level is one of the major challenges. As the dimensions shrink, it becomes increasingly difficult to sputter-deposit pinhole-free copper seed layers for electrodeposition of copper. In this circumstance, CVD/ALD of copper as a seed layer for electrodeposition or for the fill of the finest features becomes attractive.

Chemical vapor deposition (CVD) of copper provides uniform coverage for the metallization. Atomic layer deposition (ALD), which is a modified CVD process, also provides uniform step coverage which is critical for copper seed layers. In ALD an excess amount of precursor is delivered to the deposition chamber for reaction therein to form a monolayer of reacted precursor on the wafer surface. The deposition chamber is purged with a carrier gas to remove unreacted precursor followed by the delivery of a reactant to the deposition chamber for reaction with the monolayer of reacted precursor to form the preferred material. This cycle is repeated until the desired thickness of material is achieved. Advantageously, ALD provides uniform step coverage and a high level of control over film thicknesses and as such is used extensively for the deposition of very thin films, such as diffusion barrier layers and copper seed layers, on wafer surfaces having high aspect ratio trenches and vias.

In an illustrative ALD process, sequential precursor pulses are used to form a film, layer by layer. A first precursor may be introduced to form a monolayer on a substrate, followed by introduction of a second precursor to react with the monolayer to form a first film layer. Each cycle including first and second precursor pulses therefore forms one monolayer. The process then is repeated to form successive layers until a film of desired thickness is obtained.

Digital CVD, sometimes referred to as rapid vapor deposition (RVD) is similar in nature to atomic layer deposition, involving alternate introduction of reactant gases to the substrate but without the restriction to a monolayer coverage of precursor in each cycle. Many structures can be conformally covered using a digital CVD approach with the advantage of providing faster film formation than ALD.

Liquid precursors and/or solid precursors dissolved in suitable solvents enable the direct injection and/or liquid delivery of precursors into a CVD, ALD or digital CVD vaporizer unit. The accurate and precise delivery rate can be obtained through volumetric metering to achieve reproducibility during CVD, ALD or digital CVD metallization of a VLSI device. Solid precursor delivery via specially-designed devices, such as ATMI's ProE Vap (ATMI, Danbury, Conn., USA) enables highly efficient transport of solid precursors to a CVD or ALD reactor.

Copper beta-diketonate complexes have been thoroughly investigated for use as CVD/ALD precursors, especially with fluorinated beta-diketonate ligands. These precursors can be used to deposit highly conductive, conformal films of copper. Nonetheless, when such films are integrated with Ta or TaN surfaces of the barrier material, weak adhesion is a consequence of fluorine contamination. There is therefore a need for new precursors that are free of such deficiency, without any halogengen constituents or other species that could cause poor adhesion and/or otherwise increase contact resistance with barrier materials. Accordingly, new precursors are sought, which preferably have no halogengen atoms, and as few heteroatoms (e.g., O, P, N, S) as possible.

SUMMARY OF THE INVENTION

The present invention relates to copper precursors useful in the deposition of copper and copper-containing materials, e.g., on microelectronic device substrates by techniques such as chemical vapor deposition (CVD), atomic layer deposition (ALD) and digital CVD, and to precursor formulations containing such precursors.

In one aspect, the invention relates to a copper precursor compound selected from the group consisting of compounds of formulae (i)-(xvii):

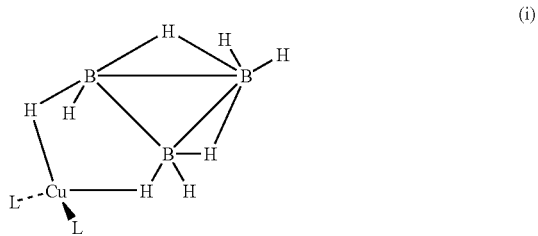

wherein each L may be the same as or different from the other, each is a unidentate or multidentate Lewis-base ligand, and each is independently selected from the group consisting of phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and hetero-carbenes;

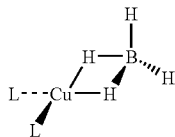

(ii)

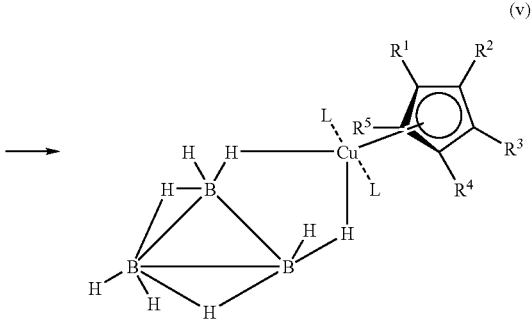

(v)

wherein each L may be the same as or different from the other, each is a unidentate or multidentate Lewis-base ligand, and each is independently selected from the group consisting of phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and hetero-carbenes;

wherein each of $R^1$, $R^2$, $R^3$, $R^4$ and $R^5$ may be the same as or different from the others, and each is independently selected from among hydrogen, $C_1$-$C_6$ alkyl, $C_2$-$C_6$ alkenyl, $C_6$-$C_{10}$ aryl, $C_1$-$C_6$ alkoxy, $C_3$-$C_6$ alkylsilyl, $C_1$-$C_6$ alkylamino, hydrazino of the formula $R_aR_bNNR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, such as, for example, aminoalkyl, alkoxyalkyl, aryloxyalkyl, imidoalkyl, and acetylalkyl, wherein suitable groups in these classes include those of the following formulae:

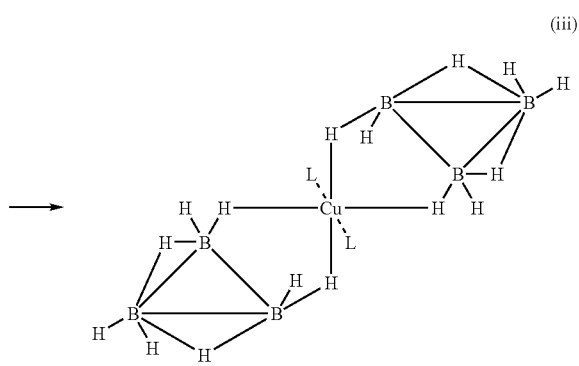

(iii)

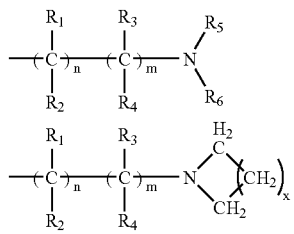

aminoalkyls wherein each L may be the same as or different from the other, each is a unidentate or multidentate Lewis-base ligand, and each is independently selected from the group consisting of phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and hetero-carbenes;

wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

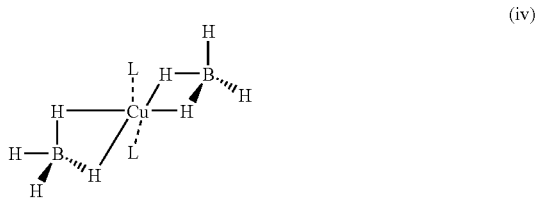

(iv)

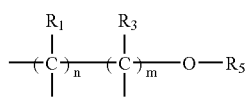

alkoxyalkyls and aryloxyalkyls wherein each L may be the same as or different from the other, each is a unidentate or multidentate Lewis-base ligand, and each is independently selected from the group consisting of phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and hetero-carbenes;

wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time; each L may be the same as or different from the other, each is a unidentate or multidentate Lewis-base ligand, and each is independently selected from the group consisting of phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and hetero-carbenes;

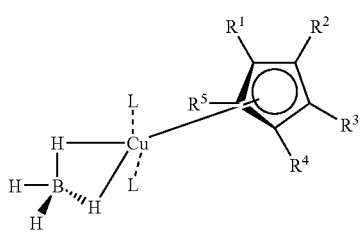

(vi)

wherein each of $R^1$, $R^2$, $R^3$, $R^4$ and $R^5$ may be the same as or different from the others, and each is independently selected from among hydrogen, $C_1$-$C_6$ alkyl, $C_2$-$C_6$ alkenyl, $C_6$-$C_{10}$ aryl, $C_1$-$C_6$ alkoxy, $C_3$-$C_6$ alkylsilyl, $C_1$-$C_6$ alkylamino, hydrazino of the formula $R_aR_bNNR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, such as, for example, aminoalkyl, alkoxyalkyl, aryloxyalkyl, imidoalkyl, and acetylalkyl, wherein suitable groups in these classes include those of the following formulae:

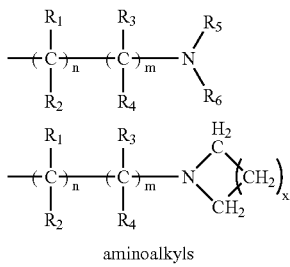

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

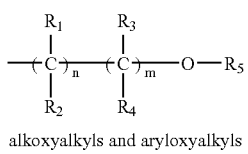

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time; each L may be the same as or different from the other, each is a unidentate or multidentate Lewis-base ligand, and each is independently selected from the group consisting of phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and hetero-carbenes;

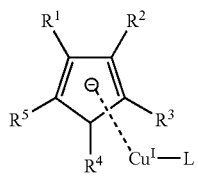

(vii)

wherein each of $R^1$, $R^2$, $R^3$, $R^4$ and $R^5$ may be the same as or different from the others, and each is independently selected from among hydrogen, $C_1$-$C_6$ alkyl, $C_2$-$C_6$ alkenyl, $C_6$-$C_{10}$ aryl, $C_1$-$C_6$ alkoxy, $C_3$-$C_6$ alkylsilyl, $C_1$-$C_6$ alkylamino, hydrazino of the formula $R_aR_bNNR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, such as, for example, aminoalkyl, alkoxyalkyl, aryloxyalkyl, imidoalkyl, and acetylalkyl, wherein suitable groups in these classes include those of the following formulae:

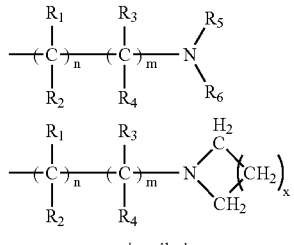

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

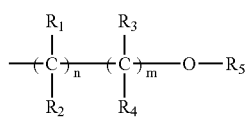

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time; each L may be the same as or different from the other, each is a unidentate or multidentate Lewis-base ligand, and each is independently selected from the group consisting of phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and hetero-carbenes;

(viii)

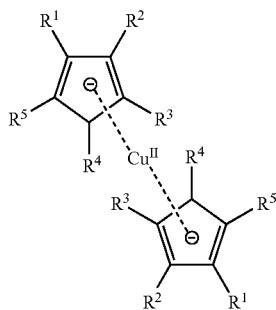

wherein each of $R^1$, $R^2$, $R^3$, $R^4$ and $R^5$ may be the same as or different from the others, and each is independently selected from among hydrogen, $C_1$-$C_6$ alkyl, $C_2$-$C_6$ alkenyl, $C_6$-$C_{10}$ aryl, $C_1$-$C_6$ alkoxy, $C_3$-$C_6$ alkylsilyl, $C_1$-$C_6$ alkylamino, hydrazino of the formula $R_aR_bNNR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, such as, for example, aminoalkyl, alkoxyalkyl, aryloxyalkyl, imidoalkyl, and acetylalkyl, wherein suitable groups in these classes include those of the following formulae:

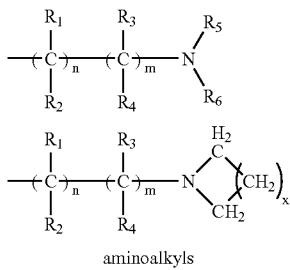

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

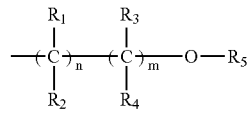

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time;

(ix)

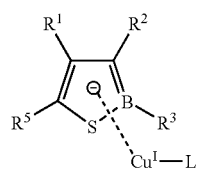

hydrogen, $C_1$-$C_6$ alkyl, $C_2$-$C_6$ alkenyl, $C_6$-$C_{10}$ aryl, $C_1$-$C_6$ alkoxy, $C_3$-$C_6$ alkylsilyl, $C_1$-$C_6$ amino, hydrazino of the formula $R_aR_bNNR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, such as, for example, aminoalkyl, alkoxyalkyl, aryloxyalkyl, imidoalkyl, and acetylalkyl, wherein suitable groups in these classes include those of the following formulae:

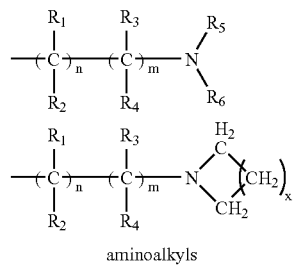

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

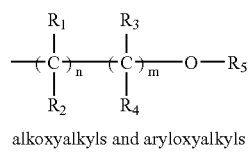

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time; L is a unidentate or multidentate Lewis-base ligand selected from among phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and hetero-carbenes;

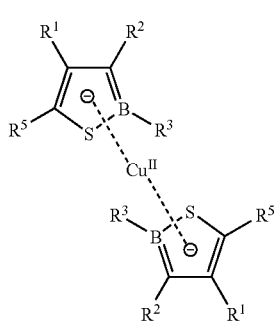

(x)

wherein each of $R^1$, $R^2$, $R^3$, $R^4$ and $R^5$ may be the same as or different from the others, and each is independently selected from among hydrogen, $C_1$-$C_6$ alkyl, $C_2$-$C_6$ alkenyl, $C_6$-$C_{10}$ aryl, $C_1$-$C_6$ alkoxy, $C_3$-$C_6$ alkylsilyl, $C_1$-$C_6$ alkylamino, hydrazino of the formula $R_aR_bNNR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, such as, for example, aminoalkyl, alkoxyalkyl, aryloxyalkyl, imidoalkyl, and acetylalkyl, wherein suitable groups in these classes include those of the following formulae:

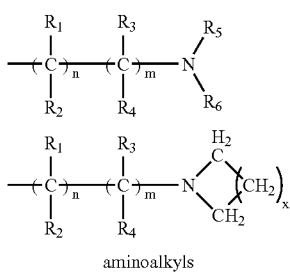

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

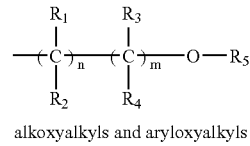

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time;

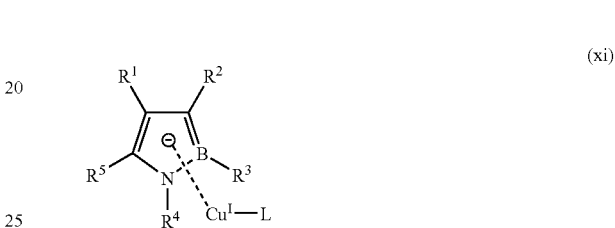

(xi)

wherein each of $R^1$, $R^2$, $R^3$, $R^4$ and $R^5$ may be the same as or different from the others, and each is independently selected from among hydrogen, $C_1$-$C_6$ alkyl, $C_2$-$C_6$ alkenyl, $C_6$-$C_{10}$ aryl, $C_1$-$C_6$ alkoxy, $C_3$-$C_6$ alkylsilyl, $C_1$-$C_6$ amino, hydrazino of the formula $R_aR_bNNR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, such as, for example, aminoalkyl, alkoxyalkyl, aryloxyalkyl, imidoalkyl, and acetylalkyl, wherein suitable groups in these classes include those of the following formulae:

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

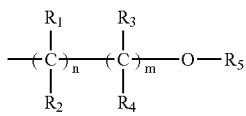

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time; L is a unidentate or multidentate Lewis-base ligand selected from among phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and hetero-carbenes;

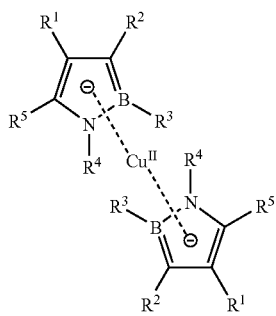

(xii)

wherein each of $R^1$, $R^2$, $R^3$, $R^4$ and $R^5$ may be the same as or different from the others, and each is independently selected from among hydrogen, $C_1$-$C_6$ alkyl, $C_1$-$C_6$ alkenyl, $C_6$-$C_{10}$ aryl, $C_1$-$C_6$ alkoxy, $C_3$-$C_6$ alkylsilyl, $C_1$-$C_6$ amino, hydrazino of the formula $R_aR_bNNR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, such as, for example, aminoalkyl, alkoxyalkyl, aryloxyalkyl, imidoalkyl, and acetylalkyl, wherein suitable groups in these classes include those of the following formulae:

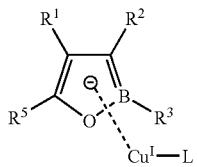

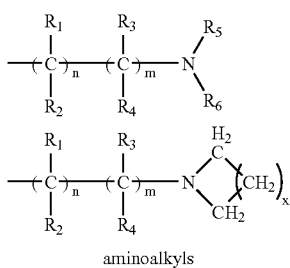

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

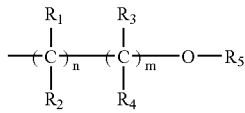

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time;

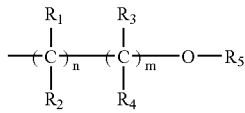

(xiii)

hydrogen, $C_1$-$C_6$ alkyl, $C_1$-$C_6$ alkenyl, $C_6$-$C_{10}$ aryl, $C_1$-$C_6$ alkoxy, $C_3$-$C_6$ alkylsilyl, $C_1$-$C_6$ amino, hydrazino of the formula $R_aR_bNNR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, such as, for example, aminoalkyl, alkoxyalkyl, aryloxyalkyl, imidoalkyl, and acetylalkyl, wherein suitable groups in these classes include those of the following formulae:

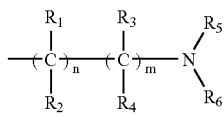

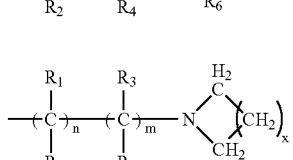

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

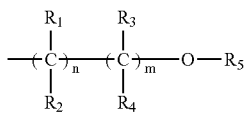

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time; L is a unidentate or multidentate Lewis-base ligand selected from among phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and hetero-carbenes;

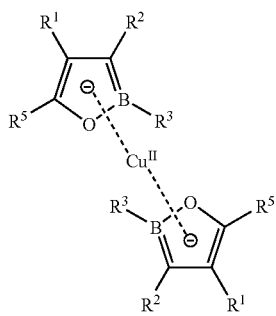 (xiv)

wherein each of $R^1$, $R^2$, $R^3$, $R^4$ and $R^5$ may be the same as or different from the others, and each is independently selected from among hydrogen, $C_1$-$C_6$ alkyl, $C_1$-$C_6$ alkenyl, $C_6$-$C_{10}$ aryl, $C_1$-$C_6$ alkoxy, $C_3$-$C_6$ alkylsilyl, $C_1$-$C_6$ amino, hydrazino of the formula $R_aR_bNNR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, such as, for example, aminoalkyl, alkoxyalkyl, aryloxyalkyl, imidoalkyl, and acetylalkyl, wherein suitable groups in these classes include those of the following formulae:

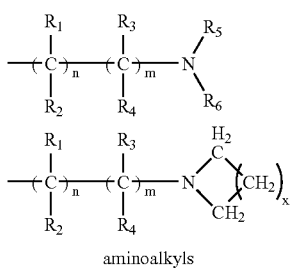

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

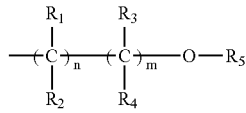

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time;

$$CuHL_n \quad (xv)$$

wherein n is an integer having a value of from 0 to 2 inclusive, and each L may be the same as or different from other(s), each is a unidentate or multidentate Lewis-base ligand, and each is independently selected from the group consisting of phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and hetero-carbenes; and

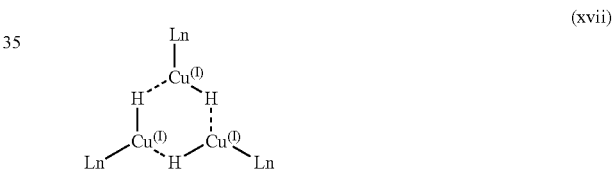 (xvii)

wherein n is an integer having a value of from 0 to 2 inclusive, and each L may be the same as or different from the other, each is a unidentate or multidentate Lewis-base ligand, and each is independently selected from the group consisting of phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and hetero-carbenes.

In another aspect, the invention relates to a copper precursor formulation comprising a copper precursor compound of the invention, and a solvent medium.

In a further aspect, the invention relates to a precursor vapor composition, comprising a vapor of a copper precursor compound of the invention.

A further aspect of the invention relates to a reagent source package, comprising a storage and dispensing vessel containing a copper precursor compound of the invention.

A still further aspect of the invention relates to a method of making a copper borohydride compound, comprising a reaction step selected from the following group of reaction steps:

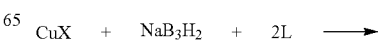

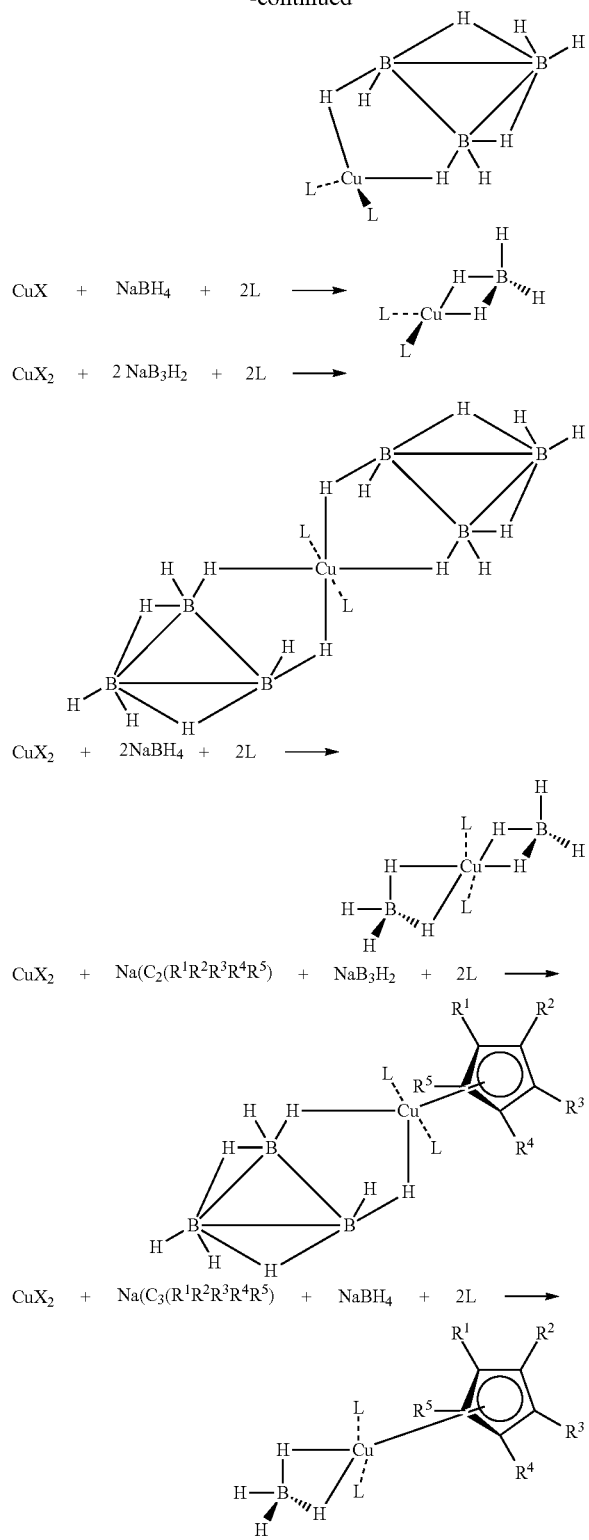

and pendant ligands including functional group(s) providing further coordination to the metal center, such as, for example, aminoalkyl, alkoxyalkyl, aryloxyalkyl, imidoalkyl, and acetylalkyl, wherein suitable groups in these classes include those of the following formulae:

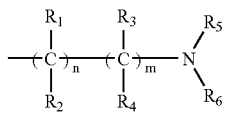

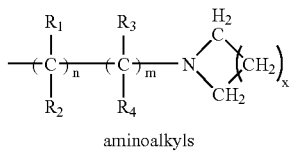

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

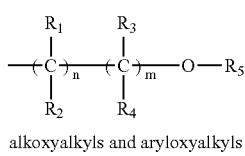

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time; each L may be the same as or different from the other, each is a unidentate or multidentate Lewis-base ligand, and each is independently selected from the group consisting of phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and hetero-carbenes; and X is halogen.

An additional aspect of the invention relates to a method of making a cyclopentadienyl-type copper precursor, comprising carrying out a synthesis selected from a synthetic route comprising wherein each of $R^1$, $R^2$, $R^3$, $R^4$ and $R^5$ may be the same as or different from the others, and each is independently selected from among hydrogen, $C_1$-$C_6$ alkyl, $C_2$-$C_6$ alkenyl, $C_6$-$C_{10}$ aryl, $C_1$-$C_6$ alkoxy, $C_3$-$C_6$ alkylsilyl, $C_1$-$C_6$ alkylamino, hydrazino of the formula $R_aR_bNNR_c$— wherein each of $R_a$, $R_b$ and $R_c$ may be the same as or different from one another and each is independently selected from among $C_1$-$C_6$ alkyl,

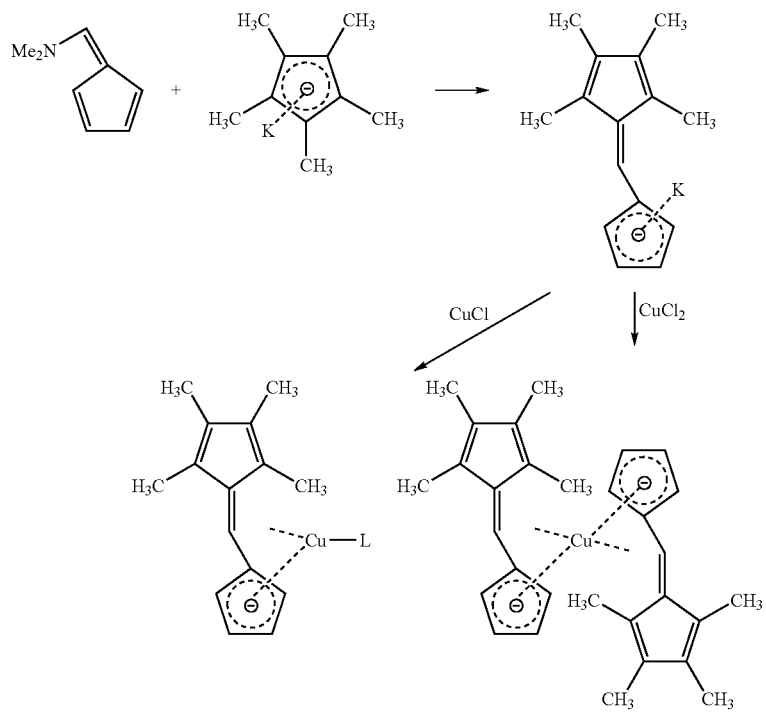

and recovering the cyclopentadienyl-type copper precursor from a reaction volume including reactants and products of such synthesis. Such synthesis may be carried out with the cyclopentadienyl substituents instead of being all methyl are each independently selected from among hydrogen, $C_1$-$C_6$ alkyl, $C_1$-$C_6$ alkenyl, $C_6$-$C_{10}$ aryl, $C_1$-$C_6$ alkoxy, $C_3$-$C_6$ alkylsilyl, $C_1$-$C_6$ amino, hydrazino of the formula $R_aR_bNNR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, such as, for example, aminoalkyl, alkoxyalkyl, aryloxyalkyl, imidoalkyl, and acetylalkyl, wherein suitable groups in these classes include those of the following formulae:

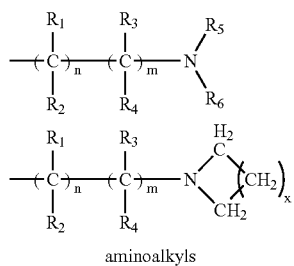

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

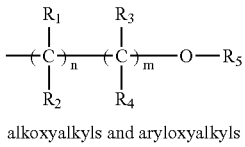

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time; and with L being a unidentate or multidentate Lewis-base ligand selected from the group consisting of phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and hetero-carbenes.

The invention in a further aspect relates to a method of making a copper hydride compound, comprising carrying out a synthesis including the following reaction:

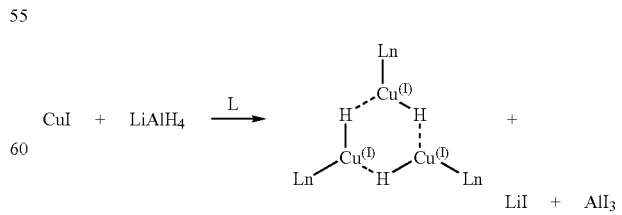

wherein n is an integer having a value of from 0 to 2 inclusive, and each L may be the same as or different from other(s), and each L is independently selected from the group consisting of phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and hetero-carbenes.

Still another aspect of the invention relates to a copper precursor compound selected from the group consisting of $(Ph_3P)_2CuBH_4$, CpCu(CyNC), EtCpCu(tBuNC), and MeCpCu(tBuNC), wherein Ph is phenyl, Cp is cyclopentadienyl, Cy is cyclohexyl, Et is ethyl, and tBu is tertiary butyl.

As used herein, the designation of organic substituents by reference to carbon numbers, includes ranges as well as sub-ranges within the ranges identified by end-point carbon numbers, and such sub-ranges may be specified, e.g., as including one of such end-point carbon numbers in such a sub-range, or as including carbon numbers greater than the lower end-point carbon number and less than the upper end-point carbon number of the range, to constitute various sub-ranges in the various specific embodiments of the invention. Hydrocarbon groups may be branched or unbranched.

Other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
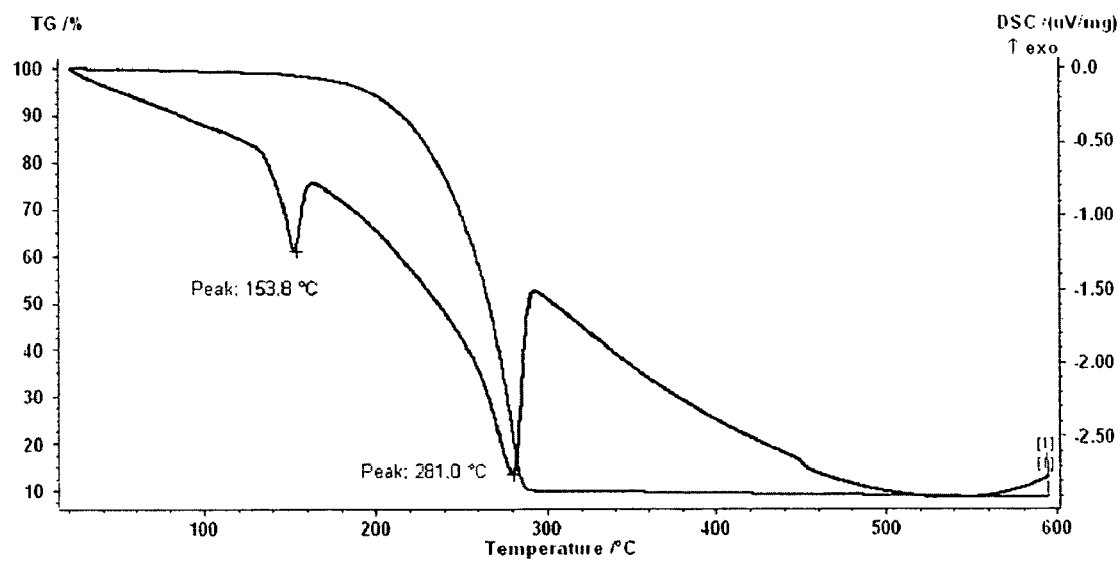
FIG. 1 is a simultaneous thermal analysis (STA) plot for $(Ph_3P)_2CuBH_4$.

The present invention relates to copper precursors that have utility in deposition of copper by film deposition techniques such as chemical vapor deposition (CVD), atomic layer deposition (ALD) and rapid vapor deposition (digital CVD). Such precursors include various specific copper precursors that contain halogengen substituents, as well as various other copper precursors that are free of halogengen atoms (F, Cl, Br, I). From such precursors, copper can be deposited on substrates, e.g., microelectronic device substrates, at temperatures below 500° C.

The precursors of the invention can be used for metallization of integrated circuitry with copper. In specific embodiments, these precursors can be employed to form copper thin films on barrier layers in microelectronic device structures, such as on the lower interconnect level in such device structures.

One class of copper precursors of the invention include is constituted by copper borohydrides. This class of copper precursors of the invention includes compounds having the structures set out in Table 1 below, which are shown with an appertaining synthesis reaction.

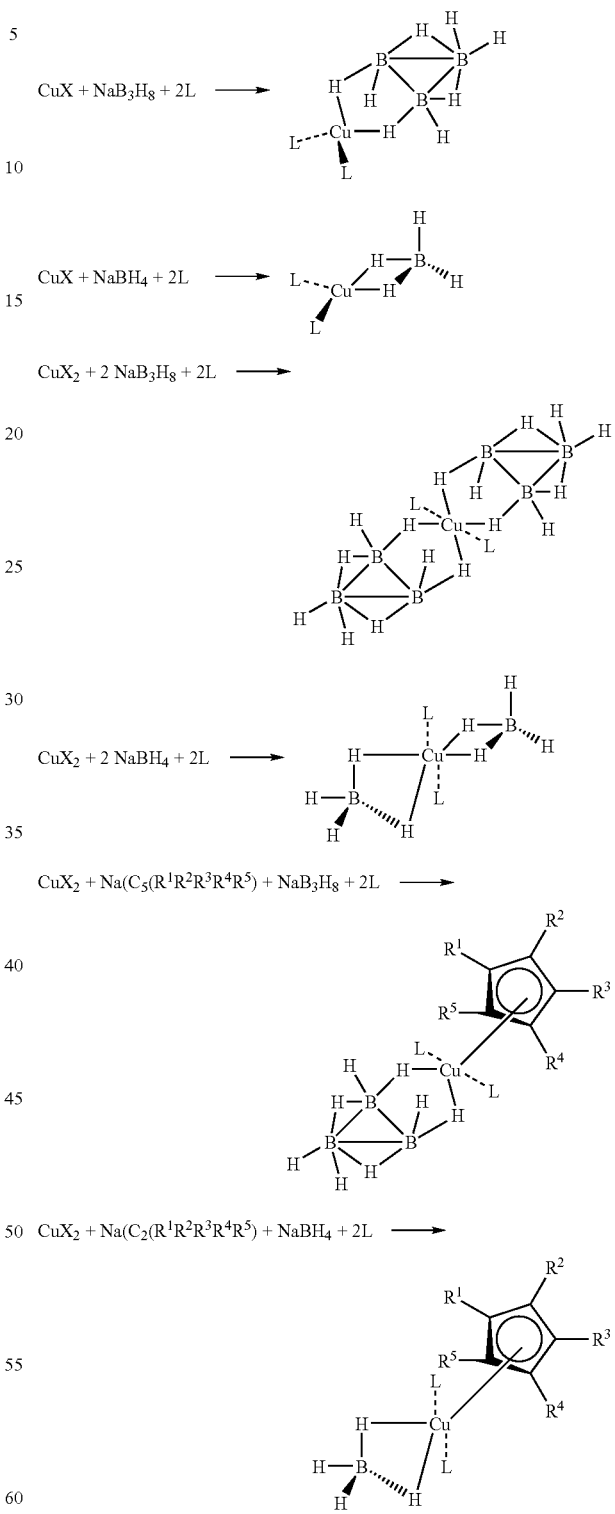

TABLE 1

Copper Borohydride Precursors

In the compounds and synthetic reactions shown in Table 1, X is halogen (fluoro, chloro, bromo or iodo); each of $R^1$, $R^2$, $R^3$, $R^4$ and $R^5$ may be the same as or different from the others, and each is independently selected from among hydrogen, $C_1$-$C_6$ alkyl, $C_2$-$C_6$ alkenyl, $C_6$-$C_{10}$ aryl, $C_1$-$C_6$ alkoxy, $C_3$-$C_6$ alkylsilyl, $C_1$-$C_6$ alkylamino, hydrazino of the formula $R_aR_bN$-$NR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, such as, for example, aminoalkyl, alkoxyalkyl, aryloxyalkyl, imidoalkyl, and acetylalkyl, wherein suitable groups in these classes include those of the following formulae:

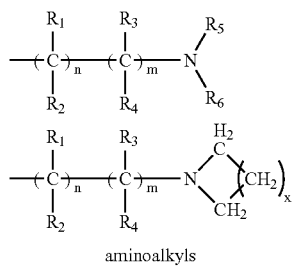

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

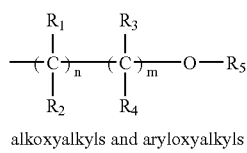

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time; each L may be the same as or different from the other, each is a unidentate or multidentate Lewis-base ligand, and each is independently selected from the group consisting of phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and hetero-carbenes.

The class of copper precursors shown in Table 1 can be varied by selection and synthesis of particular borohydride ligands that are coordinated to the copper central atom, so that the resulting precursor possesses a thermal and solution behavior that is tailored for the specific deposition process in which the precursor is employed.

The synthetic reactions shown in Table 1 are of an illustrative character only, and other synthetic routes and reagents can be employed, within the skill of the art, based on the disclosure herein.

The copper precursors of Table 1 are usefully employed as precursors for copper deposition using CVD, ALD or digital CVD deposition processes, under process conditions that can readily empirically be determined, to achieve deposited copper of a desired character, e.g., film thickness, conformality, etc.

As a specific example of the thermal properties of an illustrative compound within the scope of the general formula compounds of Table 1, a simultaneous thermal analysis (STA) plot for $(Ph_3P)_2CuBH_4$ is shown in FIG. 1 hereof. In this graph, the differential scanning calorimetry (DSC) curve shows peaks at 153.8° C. and 281.0° C. The compound evidenced good transport properties (the T50 value was 267° C.) and the thermogravimetric (TG) curve shows a low mass residue (MR) of 8.55% for the 7.844 mg sample used in the thermal properties characterization.

Another class of copper precursors of the invention include is constituted by the copper compounds having cyclopentadienyl-type ligands, of the formulae A, A', B, B', C, C', D, and D' shown in Table II below.

TABLE II

Copper Precursors Having Cyclopentadienyl-Type Ligands

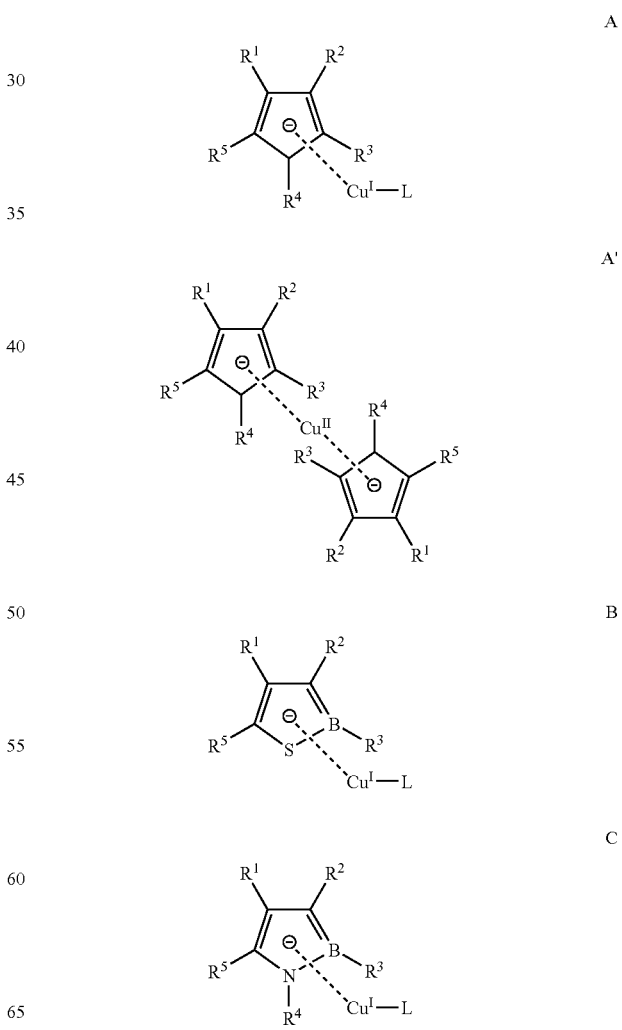

TABLE II-continued

Copper Precursors Having Cyclopentadienyl-Type Ligands

A'

B

C

D'

In such formulae A, A', B, B', C, C', D, and D', each of $R^1$, $R^2$, $R^3$, $R^4$ and $R^5$ may be the same as or different from the others, and each is independently selected from among hydrogen, $C_1$-$C_6$ alkyl, $C_2$-$C_6$ alkenyl, $C_6$-$C_{10}$ aryl, $C_1$-$C_6$ alkoxy, $C_3$-$C_6$ alkylsilyl, $C_1$-$C_6$ amino, hydrazino of the formula $R_aR_bN$-$NR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, such as, for example, aminoalkyl, alkoxyalkyl, aryloxyalkyl, imidoalkyl, and acetylalkyl, wherein suitable groups in these classes include those of the following formulae:

D

D' aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

C' alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time; each L may be the same as or different from the other, each is a unidentate or multidentate Lewis-base ligand, and each is independently selected from the group consisting of phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and hetero-carbenes.

The electron-deficient character of the cyclopentadienyl-like ligands in the compounds of formulae B, B', C, C', D, D' due to the presence of boron atom is advantageous in bonding to the electron-rich copper central atom.

The class of copper precursors shown in Table 2 can be varied by selection and synthesis of particular cyclopentadienyl-type (Cp-type) ligands that are coordinated to the copper central atom, so that the resulting precursor possesses a thermal and solution behavior that is suitably tailored for the specific deposition process in which such precursor is employed.

The copper precursors of Table 2 thus constitute a class of compounds including: substituted cyclopentadienyl compounds A of the formula $(C_5R^1R^2R^3R^4R^5)$CuL wherein each of $R^1$, $R^2$, $R^3$, $R^4$ and $R^5$ may be the same as or different from the others, and each is independently selected from among hydrogen, $C_1$-$C_6$ alkyl, $C_2$-$C_6$ alkenyl, $C_6$-$C_{10}$ aryl, $C_1$-$C_6$ alkoxy, $C_3$-$C_6$ alkylsilyl, $C_1$-$C_6$ amino, hydrazino of the formula $R_aR_bNNR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, such as, for example, aminoalkyl, alkoxyalkyl, aryloxyalkyl, imidoalkyl, and acetylalkyl, wherein suitable groups in these classes include those of the following formulae:

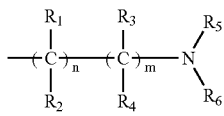

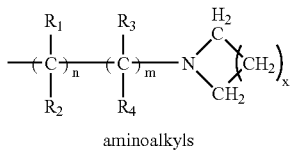

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

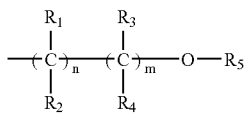

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time; L is a unidentate or multidentate Lewis-base ligand selected from among phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and hetero-carbenes;

substituted cyclopentadienyl compounds A' of the formula $(C_5R^1R^2R^3R^4R^5)_2Cu$ wherein each of $R^1$, $R^2$, $R^3$, $R^4$ and $R^5$ may be the same as or different from the others, and each is independently selected from among hydrogen, $C_1$-$C_6$ alkyl, $C_1$-$C_6$ alkenyl, $C_6$-$C_{10}$ aryl, $C_1$-$C_6$ alkoxy, $C_3$-$C_6$ alkylsilyl, $C_1$-$C_6$ amino, hydrazino of the formula $R_aR_bNNR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, such as, for example, aminoalkyl, alkoxyalkyl, aryloxyalkyl, imidoalkyl, and acetylalkyl, wherein suitable groups in these classes include those of the following formulae:

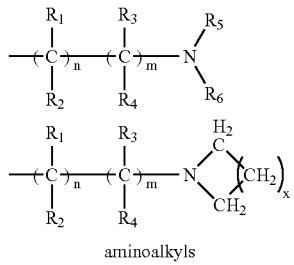

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

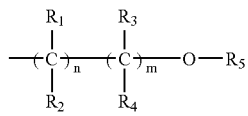

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time;

thiaborolyl compounds B of the formula $(C_3BSR^1R^2R^3R^5)$CuL wherein each of $R^1$, $R^2$, $R^3$, $R^4$ and $R^5$ may be the same as or different from the others, and each is independently selected from among hydrogen, $C_1$-$C_6$ alkyl, $C_1$-$C_6$ alkenyl, $C_6$-$C_{10}$ aryl, $C_1$-$C_6$ alkoxy, $C_3$-$C_6$ alkylsilyl, $C_1$-$C_6$ amino, hydrazino of the formula $R_aR_bNNR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, such as, for example, aminoalkyl, alkoxyalkyl, aryloxyalkyl, imidoalkyl, and acetylalkyl, wherein suitable groups in these classes include those of the following formulae:

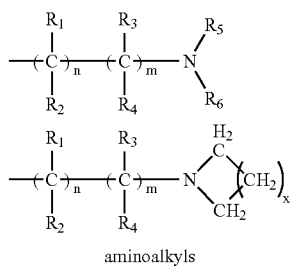

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

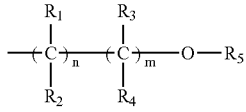

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time; and L is a unidentate or multidentate Lewis-base ligand selected from among phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and hetero-carbenes; thiaborolyl compounds B' of the formula $(C_3BSR^1R^2R^3R^5)_2Cu$ wherein each of $R^1$, $R^2$, $R^3$, $R^4$ and $R^5$ may be the same as or different from the others, and each is independently selected from among hydrogen, $C_1$-$C_6$ alkyl, $C_1$-$C_6$ alkenyl, $C_6$-$C_{10}$ aryl, $C_1$-$C_6$ alkoxy, $C_3$-$C_6$ alkylsilyl, $C_1$-$C_6$ amino, hydrazino of the formula $R_aR_bN$-$NR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, such as, for example, aminoalkyl, alkoxyalkyl, aryloxyalkyl, imidoalkyl, and acetylalkyl, wherein suitable groups in these classes include those of the following formulae:

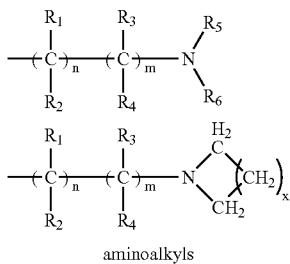

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

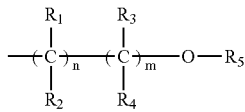

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time; azaborolyl compounds C of the formula $(C_3BNR^1R^2R^3R^4R^5)CuL$ wherein each of $R^1$, $R^2$, $R^3$, $R^4$ and $R^5$ may be the same as or different from the others, and each is independently selected from among hydrogen, $C_1$-$C_6$ alkyl, $C_2$-$C_6$ alkenyl, $C_6$-$C_{10}$ aryl, $C_1$-$C_6$ alkoxy, $C_3$-$C_6$ alkylsilyl, $C_1$-$C_6$ amino, hydrazino of the formula $R_aR_bN$-$NR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, such as, for example, aminoalkyl, alkoxyalkyl, aryloxyalkyl, imidoalkyl, and acetylalkyl, wherein suitable groups in these classes include those of the following formulae:

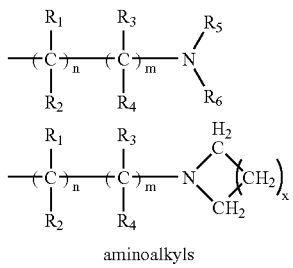

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

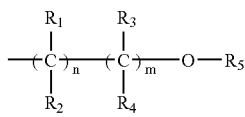

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time; L is a unidentate or multidentate Lewis-base ligand selected from among phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and hetero-carbenes;

azaborolyl compounds C' of the formula $(C_3BNR^1R^2R^3R^4R^5)_2Cu$ wherein each of $R^1$, $R^2$, $R^3$, $R^4$ and $R^5$ may be the same as or different from the others, and each is independently selected from among hydrogen, $C_1$-$C_6$ alkyl, $C_2$-$C_6$ alkenyl, $C_6$-$C_{10}$ aryl, $C_1$-$C_6$ alkoxy, $C_3$-$C_6$ alkylsilyl, $C_1$-$C_6$ amino, hydrazino of the formula $R_aR_bNNR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, such as, for example, aminoalkyl, alkoxyalkyl, aryloxyalkyl, imidoalkyl, and acetylalkyl, wherein suitable groups in these classes include those of the following formulae:

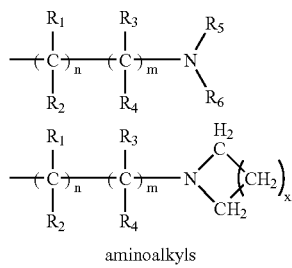

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

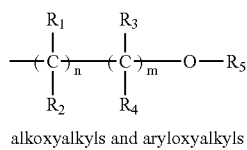

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time;

oxoborolyl compounds D of the formula $(C_3BOR^1R^2R^3R^5)$CuL wherein each of $R^1$, $R^2$, $R^3$, $R^4$ and $R^5$ may be the same as or different from the others, and each is independently selected from among hydrogen, $C_1$-$C_6$ alkyl, $C_2$-$C_6$ alkenyl, $C_6$-$C_{10}$ aryl, $C_1$-$C_6$ alkoxy, $C_3$-$C_6$ alkylsilyl, $C_1$-$C_6$ amino, hydrazino of the formula $R_aR_bNNR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, such as, for example, aminoalkyl, alkoxyalkyl, aryloxyalkyl, imidoalkyl, and acetylalkyl, wherein suitable groups in these classes include those of the following formulae:

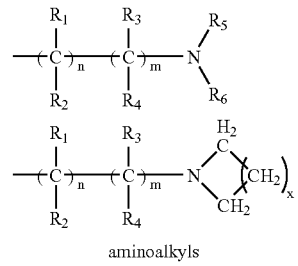

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

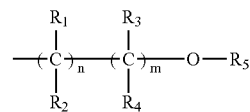

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time; L is a unidentate or multidentate Lewis-base ligand selected from among phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and hetero-carbenes; and oxoborolyl compounds D' of the formula $(C_3BOR^1R^2R^3R^5)_2Cu$ wherein each of $R^1$, $R^2$, $R^3$, $R^4$ and $R^5$ may be the same as or different from the others, and each is independently selected from among hydrogen, $C_1$-$C_6$ alkyl, $C_2$-$C_6$ alkenyl, $C_6$-$C_{10}$ aryl, $C_1$-$C_6$ alkoxy, $C_3$-$C_6$ alkylsilyl, $C_1$-$C_6$ amino, hydrazino of the formula $R_aR_bNNR_c$— wherein each of $R^a$, $R_b$ and $R_c$ may be the same as or different from one another and each is independently selected from among $C_1$-$C_6$ alkyl, and pendant ligands including functional group(s) providing further coordination to the metal center, such as, for example, aminoalkyl, alkoxyalkyl, aryloxyalkyl, imidoalkyl, and acetylalkyl, wherein suitable groups in these classes include those of the following formulae:

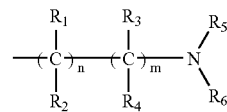

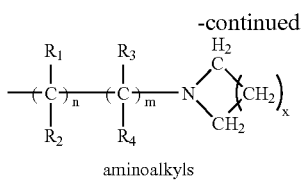

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

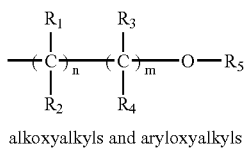

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time.

The foregoing copper precursors of formulae A, A', B, B', C, C', D, and D' are usefully employed as precursors for copper deposition using CVD, ALD or digital CVD deposition processes, under process conditions that can readily empirically be determined, to achieve deposited copper of a desired character, e.g., film thickness, conformality, etc.

Set out in Table 3 below is an illustrative synthesis scheme for compounds of formulae A and A'.

TABLE 3

Synthetic Route for Formula A and A' Copper Precursors

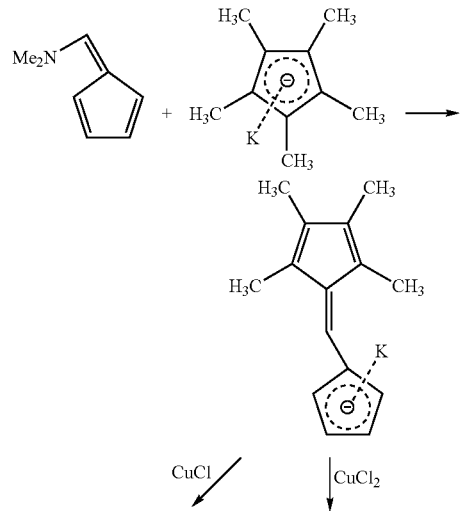

TABLE 3-continued

Synthetic Route for Formula A and A' Copper Precursors

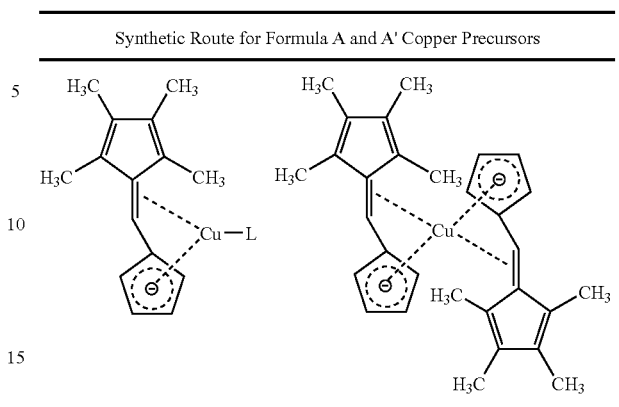

wherein L is selected from among phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and hetero-carbenes, and wherein such synthesis may be carried out with the cyclopentadienyl substituents instead of being all methyl are each independently selected from among hydrogen, $C_1$-$C_6$ alkyl, $C_1$-$C_6$ alkenyl, $C_6$-$C_{10}$ aryl, $C_1$-$C_6$ alkoxy, $C_3$-$C_6$ alkylsilyl, $C_1$-$C_6$ amino, hydrazino of the formula $R_aR_bNNR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, such as, for example, aminoalkyl, alkoxyalkyl, aryloxyalkyl, imidoalkyl, and acetylalkyl, wherein suitable groups in these classes include those of the following formulae:

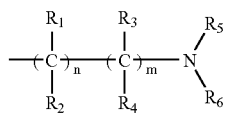

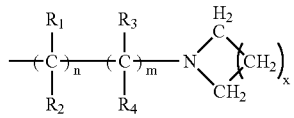

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

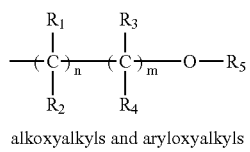

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time.

The synthetic reactions shown in Table 3 are of an illustrative character only, and other synthetic routes and reagents can be employed, within the skill of the art, based on the disclosure herein.

A further class of copper precursors of the invention comprises substituted cyclopentadienyl compounds of formula E:

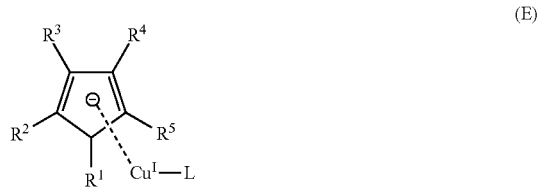

(E)

wherein each of $R^1$, $R^2$, $R^3$, $R^4$ and $R^5$ may be the same as or different from the others, and each is independently selected from among hydrogen, halogengen, $C_1$-$C_6$ alkyl, $C_1$-$C_6$ alkoxy and cyanide (—CN), and L is selected from among phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and hetero-carbenes.

These formula E compounds, $(C_5R^1R^2R^3R^4R^5)CuL$, can be readily synthesized by an alternative synthetic techniques to those discussed above in connection with the compounds of Table 2 and illustrative synthesis route of Table 3 starting with $Cu_2O$ and monomeric cyclopendienes.

Illustrative compounds of formula E include MeCpCu(tBuNC), EtCpCu(tBuNC), and CpCu(CyNC), wherein Me is methyl, Cp is cyclopentadienyl, tBu is tert-butyl, Et is ethyl and Cy is isocyanato. Characterization data for these formula E compounds are set out in FIGS. 2-7, by way of example.

Figure 2:
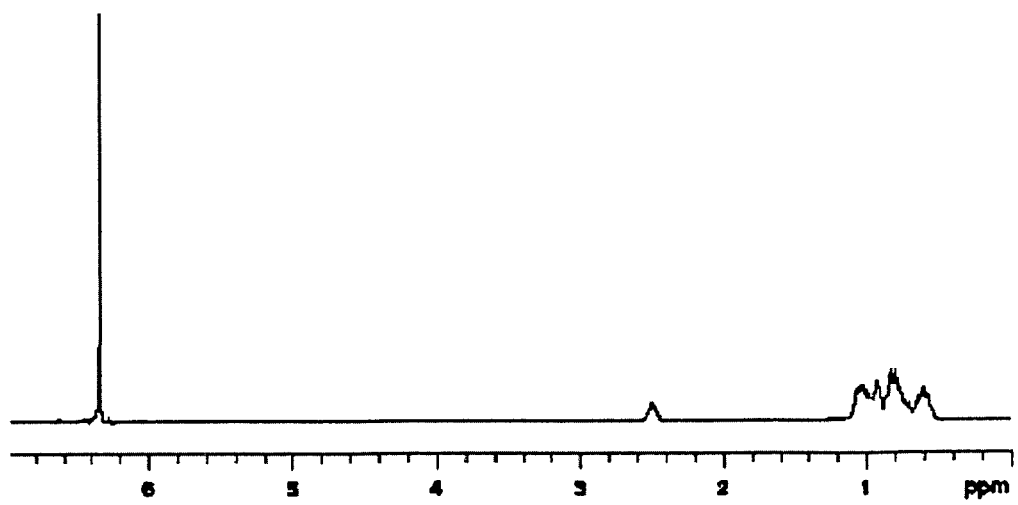
FIG. 2 is a 1H NMR plot for CpCu(CyNC).

FIG. 2 is a 1H NMR plot for CpCu(CyNC).

Figure 3:
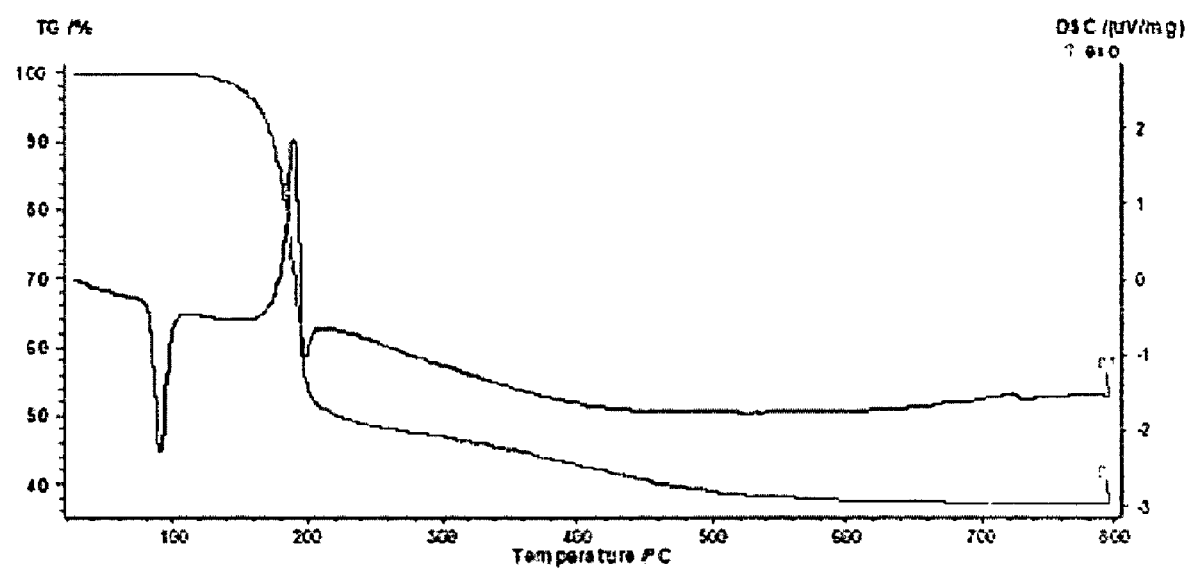
FIG. 3 is a simultaneous thermal analysis (STA) plot for CpCu(CyNC).

FIG. 3 is a simultaneous thermal analysis (STA) plot for CpCu(CyNC). In this graph, the differential scanning calorimetry (DSC) curve shows peaks in the vicinity of 90° C. and 190° C. The thermogravimetric (TG) curve shows a mass residue (MR) of 37% for the 9.90 mg sample used in the thermal properties characterization.

Figure 4:
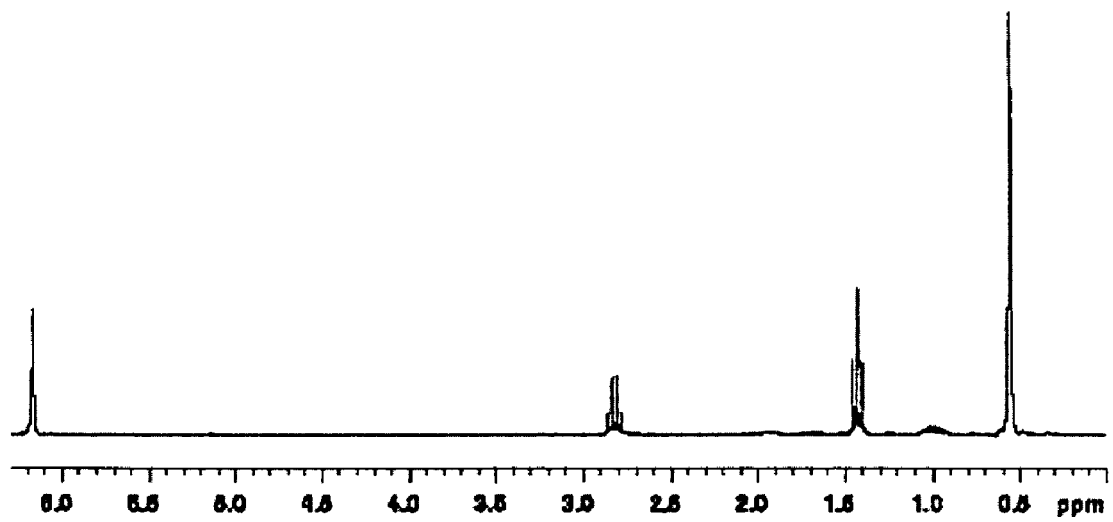
FIG. 4 is a 1H NMR plot for EtCpCu(tBuNC).

FIG. 4 is a 1H NMR plot for EtCpCu(tBuNC).

Figure 5:
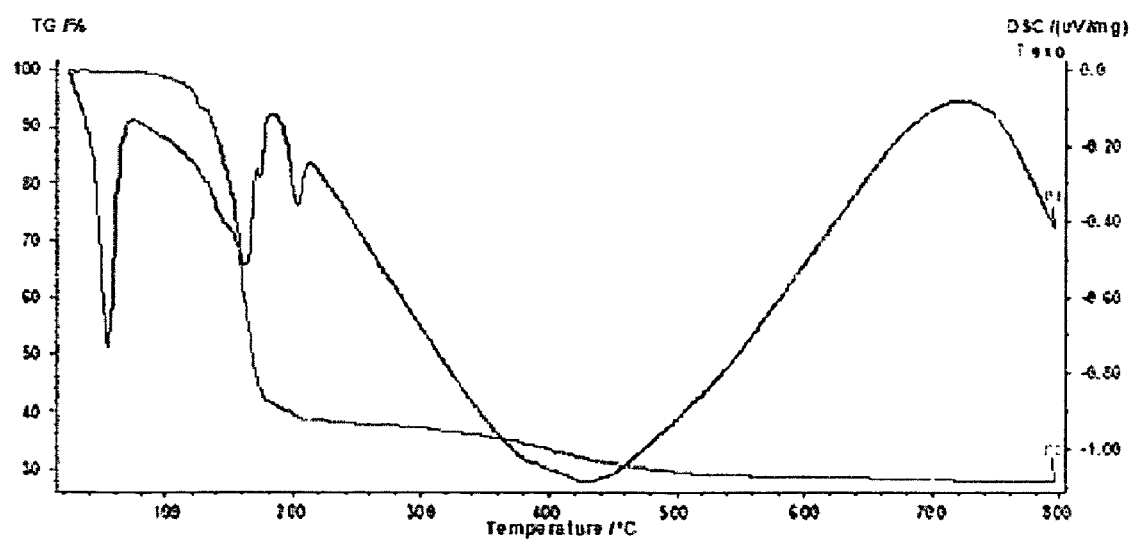
FIG. 5 is a simultaneous thermal analysis (STA) plot for CpCu(CyNC).

FIG. 5 is a simultaneous thermal analysis (STA) plot for CpCu(CyNC). In this graph, the differential scanning calorimetry (DSC) curve shows peaks in the vicinity of 55° C., 160° C. and 210° C. The thermogravimetric (TG) curve shows a mass residue (MR) of 28% for the 11.01 mg sample used in the thermal properties characterization.

Figure 6:
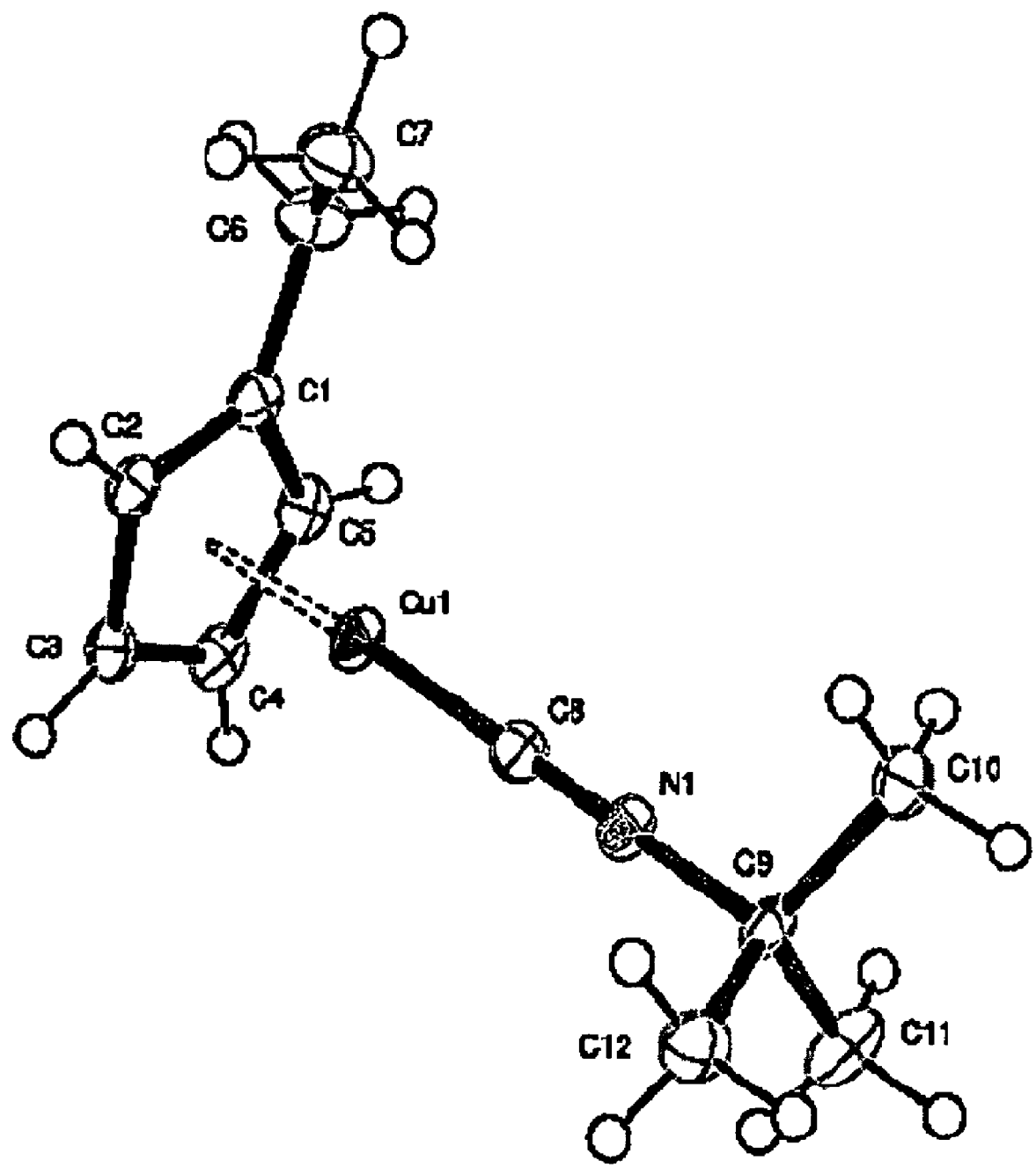
FIG. 6 is an ORTEP diagram of the structure of EtCpCu(tBuNC).

FIG. 6 is an ORTEP diagram of the structure of EtCpCu (tBuNC).

Figure 7:
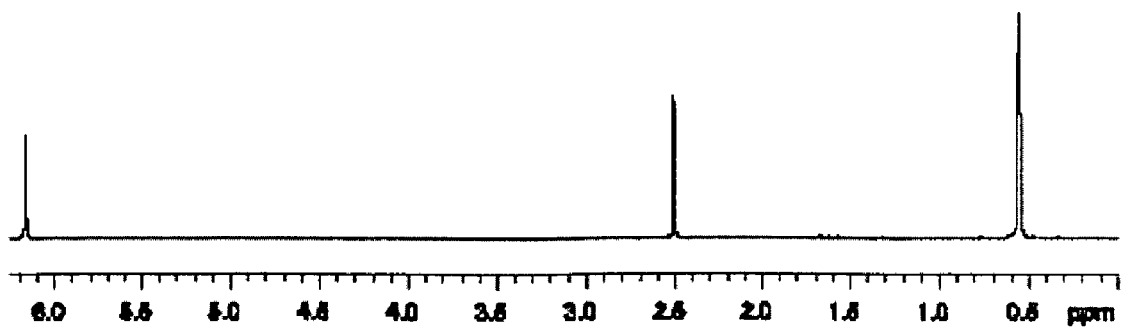
FIG. 7 is a 1H NMR plot for MeCpCu(tBuNC).

FIG. 7 is a 1H NMR plot for MeCpCu(tBuNC).

Figure 8:
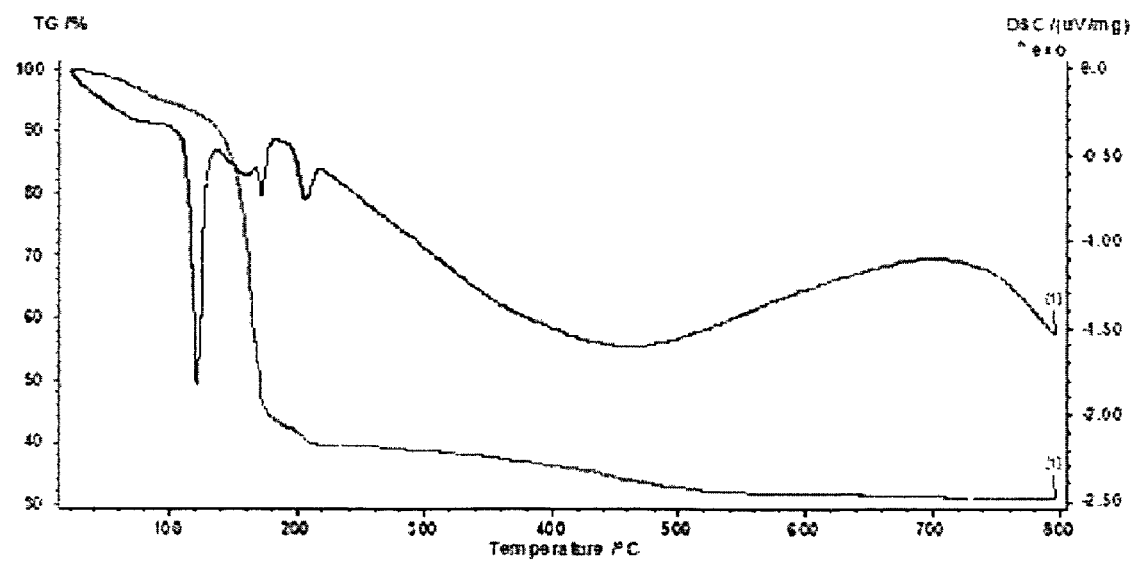
FIG. 8 is a simultaneous thermal analysis (STA) plot for MeCpCu(tBuNC).

FIG. 8 is a simultaneous thermal analysis (STA) plot for MeCpCu(tBuNC). In this graph, the differential scanning calorimetry (DSC) curve shows peaks in the vicinity of 120° C., 175° C. and 210° C. The thermogravimetric (TG) curve shows a mass residue (MR) of 31% for the 12.42 mg sample used in the thermal properties characterization.

Yet another class of copper precursors of the invention is constituted by copper hydride compounds of the formula CuHLn wherein n is an integer having a value of from 0 to 2 inclusive, and each L may be the same as or different from the other, each is a unidentate or multidentate Lewis-base ligand, and each L is independently selected from the group consisting of phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and hetero-carbenes, and n is an integer having a value of from 0 to 2 inclusive.

Such copper hydride precursors are capable of forming trimers of the formula

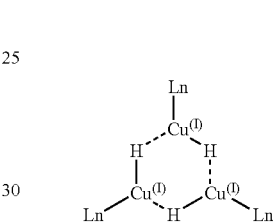

wherein each L is independently selected from the group consisting of phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and hetero-carbenes, and n is an integer having a value of from 0 to 2 inclusive.

These copper hydride monomer and trimer precursors of the invention have utility for copper deposition processes such as CVD, ALD and digital CVD, and may be utilized in solid or liquid forms that are volatilized to form corresponding precursor vapor that is contacted with the microelectronic device substrate or other suitable deposition surface to effect deposition of copper thereon.

Such copper hydride precursors in their respective monomer and trimer forms can be varied by selection and synthesis of particular ligands L that are coordinated to the copper central atom, so that the resulting precursor possesses a thermal and solution behavior that is suitably tailored for the specific deposition process in which such precursor is employed. The ligands in specific embodiments may for example be selected to provide the copper precursor with an environmentally benign or readily biodegradable character. In various embodiments of the invention, the ligand L is selected from among tertiary phosphines, azoles, imidazoles, pyridines, and bipyridines.

The copper hydride precursors described above can be synthesized in any suitable manner. In one embodiment, the aforementioned trimer copper precursors are formed by the following synthesis reaction:

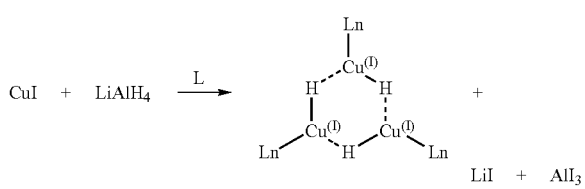

wherein each L is independently selected from the group consisting of phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and heterocarbenes, and n is an integer having a value of from 0 to 2 inclusive.

The copper precursors of the invention, as variously described herein, are usefully employed for deposition of conformal copper or copper-containing films using CVD/ALD/digital CVD techniques, as monomeric copper precursors that are transportable (volatile) at temperatures specific to such processes, e.g., temperatures below 500° C. The copper precursors of the invention can be readily synthesized from the parent ligands and the metal, to provide such precursors in readily recoverable form.

The copper precursors of the invention may be packaged in a precursor storage and dispensing package of any suitable type. Depending on the form, e.g., solid or liquid form, of the precursor, suitable storage and dispensing packages may include those described in U.S. Provisional Patent Application No. 60/662,515 filed in the names of Paul J. Marganski, et al. for "SYSTEM FOR DELIVERY OF REAGENTS FROM SOLID SOURCES THEREOF" and the storage and dispensing apparatus variously described in U.S. Pat. No. 5,518,528; U.S. Pat. No. 5,704,965; U.S. Pat. No. 5,704,967; U.S. Pat. No. 5,707,424; U.S. Pat. No. 6,101,816; U.S. Pat. No. 6,089,027; U.S. Pat. No. 7,172,646; U.S. Pat. No. 6,921,062; U.S. Pat. No. 7,300,038; and U.S. Patent application Pub. No. 2003-0111014, the disclosures of all of which are hereby incorporated herein by reference, in their respective entireties.

In CVD, ALD or digital CVD usage, the copper precursors of the invention are volatilized to form a precursor vapor that is then contacted with a microelectronic device substrate under elevated temperature vapor decomposition conditions to deposit copper on the substrate.

CVD involves the contacting of a volatile metal-organic compound in the gas phase with areas of a substrate where growth of a metal film (e.g., to form an interconnect) is required. A surface catalyzed chemical reaction, e.g., thermal decomposition, occurs and produces deposition of the desired metal. Since the metal film steadily grows on the desired surface, it is of a uniform thickness and highly conformal even to severe (e.g., high aspect) geometries. CVD is well suited to use in fabricating submicron high aspect ratio features. The copper precursors of the invention are well-suited for such CVD usage.

ALD involves the deposition of successive monolayer over a substrate within a deposition chamber typically maintained at subatmospheric pressure. An exemplary method includes feeding a single vaporized precursor into a deposition chamber to form a first monolayer over a substrate positioned therein. The substrate is heated to a temperature that is high enough to prevent condensation of the precursor but low enough to prevent thermal decomposition of said precursor. Thereafter, the flow of the first deposition precursor is ceased and an inert purge gas, e.g., nitrogen or argon, is flowed through the chamber to exhaust any unreacted first precursor from the chamber. Subsequently, a second vaporized precursor the same as or different from the first is flowed into the chamber to form a second monolayer upon the first monolayer. The second monolayer might react with the first monolayer. Additional precursors can form successive monolayer, or the above process can be repeated until a desired thickness and composition layer has been formed over the substrate. The copper precursors of the invention are well-suited for ALD processes.

Digital CVD involves the alternate introduction of reactant gases over a surface of a substrate, and is similar to ALD, but digital CVD accommodates a more rapid growth of the deposited film. In general, digital CVD achieves a rapid film growth similar to that obtained by CVD techniques, but with a high conformality of the deposited film that is characteristic of ALD techniques. The copper precursors of the invention are well-suited for digital CVD processes.

The copper precursors of the present invention are volatile and thermally stable, and are usefully employed as solid copper CVD or ALD precursors under reduced pressure deposition conditions in the CVD or ALD reactor. Alternatively, the solid precursors can be dissolved in organic solvents, and liquid delivery processes can be used to meter the solution into a vaporizer for transport of the vapor to the reactor.

The copper precursor compositions of the present invention may be used to form copper interconnect lines in microelectronic device integrated circuitry, thin-film circuitry, thin-film packaging components and thin-film recording head coils. To fabricate such integrated circuitry or thin-film circuitry, a microelectronic device substrate may be utilized having a number of dielectric and conductive layers (multilayers) formed on and/or within the substrate. The microelectronic device substrate may include a bare substrate or any number of constituent layers formed on a bare substrate. As defined herein, "microelectronic device" corresponds to semiconductor substrates, flat panel displays, and microelectromechanical systems (MEMS).

In the broad practice of the present invention, a copper-containing layer may be formed on a microelectronic device substrate using the copper precursor, for use in a first, second, third, or more metallization layer. Such copper layers typically are used in circuit locations requiring low resistivity, high performance and/or high speed circuit paths. A barrier layer may be deposited or otherwise formed on the microelectronic device substrate before a copper layer is formed on said substrate.

Using the copper precursor compositions described herein, copper can be deposited on wafer substrates using CVD, ALD or digital CVD systems, such systems being well known in the microelectronic device fabrication art. Further, water, water-generating compounds, or other adjuvants to the precursor formulation may be mixed with the copper precursor upstream of, at, or within, the CVD, ALD or digital CVD tool. Reducing agents may be utilized in an analogous fashion.

As a further variation, when copper alloy compositions are to be deposited on the substrate, the copper precursor formulation may contain or be mixed with other metal source reagent materials, or such other reagent materials may be separately vaporized and introduced to the deposition chamber.

The compositions of the present invention may be delivered to a CVD, ALD or digital CVD reactor in a variety of ways. For example, a liquid delivery system may be utilized.

Alternatively, a combined liquid delivery and flash vaporization process unit may be employed, such as the LDS300 liquid delivery and vaporizer unit (commercially available from ATMI, Inc., Danbury, Conn., USA), to enable low volatility materials to be volumetrically delivered, leading to reproducible transport and deposition without thermal decomposition of the precursor. Both of these considerations of reproducible transport and deposition without thermal decomposition are essential for providing a commercially acceptable copper CVD, ALD or digital CVD process.

In liquid delivery formulations, copper precursors that are liquids may be used in neat liquid form, or liquid or solid copper precursors may be employed in solvent formulations containing same. Thus, copper precursor formulations of the invention may include solvent component(s) of suitable character as may be desirable and advantageous in a given end use application to form copper on a substrate.

Suitable solvents may for example include alkane solvents (e.g., hexane, heptane, octane, and pentane), aryl solvents (e.g., benzene or toluene), amines (e.g., triethylamine, tert-butylamine), imines and carbodiimides (e.g., N,N'-diisopropylcarbodiimide), alcohols, ethers, ketones, aldehydes, amidines, guanadines, isoureas, and the like. The utility of specific solvent compositions for particular copper precursors may be readily empirically determined, to select an appropriate single component or multiple component solvent medium for the liquid delivery vaporization and transport of the specific copper precursor that is employed.

A wide variety of CVD, ALD or digital CVD process conditions may be employed in the use of the precursor compositions of the present invention. Generalized process conditions may include substrate temperature in a range of 50-400° C.; pressure in a range of 0.05-50 Torr; and carrier gas flows of helium, hydrogen, nitrogen, or argon in a range of 25-750 sccm, at a temperature approximately the same as the vaporizer, e.g., in a range of 50 to 120° C.

The deposition of copper thin films with useful electrical properties (low resistivity) and good adhesion to the barrier layer (e.g., formed of TiN or TaN), are also achieved by the process and precursors of the present invention. The conformality of the deposited film is practically achievable through CVD, ALD or digital CVD techniques that preferably provide a pathway to the achievement of "full-fill" copper metallization. The liquid delivery approach of the present invention, including "flash" vaporization and the use of copper precursor chemistry as herein disclosed, enable next-generation device geometries and dimensions to be attained, e.g., a conformal vertical interconnect of 22 nanometer line width. The conformal deposition of interconnects of these critical dimensions cannot be realized by currently available physical deposition methods. Thus, the approach of the present invention affords a viable pathway to future generation devices, and embodies a substantial advance in the art.

The features and advantages of the invention are more fully shown by the following illustrative and non-limiting examples.

Example 1

Synthesis of (Ethyl-tetrahapto-cyclopendienyl)(tert-butyl isocyanide) Copper (I) ((EtC$_p$)Cu(Bu$^t$NC))

A mixture of 5.0 g (34.9 mmol) of Cu$_2$O, 5.0 g (60.1 mmol) Bu$^t$NC and 23.5 g (250 mmol) of freshly cracked EtCpH was mixed at room temperature and then heated at 100° C. for an hour. After the mixture was cooled down to room temperature, 100 mL ethyl ether was added before the filtration. After the filtration, the resulting filtrate was dark yellow. Recrystallization in pentane gave 4.2 g dark yellow crude solid (EtCp)Cu(Bu$^t$NC) was obtained. (17.5 mmol, 29% overall yield based on Bu$^t$NC). Data for (EtCp)Cu(Bu$^t$NC): $^1$H NMR (benzene-d$_6$, 21° C.) (FIG. 1.1): δ 0.56 (t, 9H, —C(CH$_3$)$_3$), 1.42 (t, 3H, —CH$_2$CH$_3$), 2.24 (q, 2H, —CH$_2$CH$_3$), 6.17 (s, 5H, —C$_5$H$_5$). Anal. CuNC$_{12}$H$_{18}$: Calcd. C, 60.10%; H, 7.57%; N, 5.84%. Found: C, 59.95%; H, 7.58%; N, 5.67%.

Example 2

Synthesis of (Methyl-tetrahapto-cyclopendienyl)(tert-butyl isocyanide) Copper (I) ((MeC$_p$)Cu(Bu$^t$NC))

A mixture of 5.0 g (34.9 mmol) of Cu$_2$O, 5.0 g (60.1 mmol) Bu$^t$NC and 20.0 g (250 mmol) of freshly cracked MeCpH was mixed at room temperature and then heated at 100° C. for an hour. After the mixture was cooled down to room temperature, 100 mL ethyl ether was added before the filtration. After the filtration, the resulting filtrate was dark yellow. Recrystallization in pentane gave 3.8 g dark yellow crude solid (MeCp)Cu(Bu$^t$NC) was obtained. (16.8 mmol, 28% overall yield based on Bu$^t$NC). Data for (MeCp)Cu(Bu$^t$NC): $^1$H NMR (benzene-d$_6$, 21° C.) (FIG. 1.4): δ 0.55 (t, 9H, —C(CH$_3$)$_3$), 2.50 (s, 3H, —CH$_3$), 6.17 (s, 5H, —C$_5$H$_5$). Anal. CuNC$_{11}$H$_{16}$ Calcd. C, 58.51%; H, 7.14%; N, 6.20%. Found: C, 58.67%; H, 7.13%; N, 5.95%.

Example 3

Synthesis of (Methyl-tetrahapto-cyclopendienyl)(cyclohexyl isocyanide) Copper (I) C$_p$Cu(CyNC))

A mixture of 3.81 g (26.6 mmol) of Cu$_2$O, 5.0 g (34.9 mmol) CyNC and 12.56 g (157 mmol) of freshly cracked CpH was mixed at room temperature and then heated at 100° C. for an hour. After the mixture was cooled down to room temperature, 100 mL ethyl ether was added before the filtration. After the filtration, the resulting filtrate was dark yellow. Recrystallization in pentane gave 5.5 g dark yellow solid CpCu(CyNC) was obtained after sublimation at 120° C. under 200 mtorr vacuum. (23.0 mmol, 66% overall yield based on CyNC). Data for CpCu(CyNC): $^1$H NMR (benzene-d$_6$, 21° C.) (FIG. 1.6): δ 0.61, 0.85, 0.93, 1.08 and 2.50 (m, 11H, C$_6$H$_{11}$), 2.50 (s, 3H, —CH$_3$), 6.31 (s, 5H, —C$_5$H$_5$). Anal. CuNC$_{12}$H$_{17}$: Calcd. C, 60.35%; H, 7.17%; N, 5.87%. Found: C, 60.50%; H, 6.96%; N, 5.95%.

Example 4

Synthesis of (pentahapto-cyclopendienyl)(tert-butyl isocyanide) Copper (I) ((C$_p$Cu(Bu$^t$NC))

A mixture of 5.0 g (34.9 mmol) of Cu$_2$O, 5.0 g (60.1 mmol) Bu$^t$NC and 16.5 g (250 mmol) of freshly cracked CpH was mixed at room temperature and then heated at 70° C. for an hour. After the mixture was cooled down to room temperature, 50 mL ethyl ether was added before the filtration. After the filtration, the resulting filtrate was dark yellow. All the volatiles were pulled away in vacuo and 10 g dark yellow crude solid CpCu(Bu$^t$NC) was obtained. Sublimation at 100° C. under 200 mtorr yielded 6 g pale yellow solid (28.3 mmol, 47% overall yield based on Bu$^t$NC). Data for CpCu(Bu$^t$NC): $^1$H NMR (benzene-d$_6$, 21° C.) (FIG. 1.1): δ 0.53 (t, 9H, —C(CH$_3$)$_3$), 6.34 (s, 5H, —C$_5$H$_5$). Anal. CuNC$_{10}$H$_{14}$: Calcd. C, 56.72%; H, 6.66%; N, 6.61%. Found: C, 56.59%; H, 6.75%; N, 6.69%.

The advantages and features of the invention are further illustrated with reference to the following example, which is not to be construed as in any way limiting the scope of the invention but rather as illustrative of one embodiment of the invention in a specific application thereof.

While the invention has been has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A copper precursor composition comprising: a compound selected from the group consisting of compounds of formulae (i)-(viii):

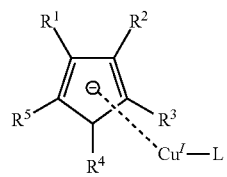

wherein each of R$^1$, R$^2$, R$^3$, R$^4$ and R$^5$ may be the same as or different from the others, and each is independently selected from among hydrogen, C$_1$-C$_6$ alkyl, C$_3$-C$_6$ alkenyl, C$_6$-C$_{10}$ aryl, C$_1$-C$_6$ alkoxy, C$_3$-C$_6$ alkylsilyl, C$_1$-C$_6$ amino, hydrazino of the formula R$_a$R$_b$NNR$_c$— wherein each of R$_a$, R$_b$ and R$_c$ may be the same as or different from one another and each is independently selected from among C$_1$-C$_6$ alkyl, and pendant ligands including functional group(s) providing further coordination to the metal center, selected from the group consisting of aminoalkyl, alkoxyalkyl, aryloxyalkyl, imidoalkyl, and acetylalkyl, and groups of the following formulae:

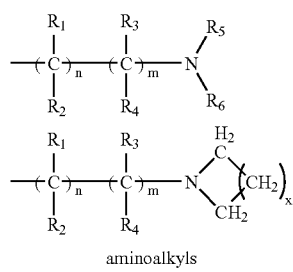

aminoalkyls wherein each of R$_1$-R$_4$ is the same as or different from one another, with each being independently selected from among hydrogen and C$_1$-C$_6$ straight chain or branched alkyl, C$_1$-C$_6$ straight chain or branched alkoxy, C$_6$-C$_{10}$ aryl and NR$_5$R$_6$; each of R$_5$ and R$_6$ is the same as or different from the other, with each being independently selected from among C$_1$-C$_6$ straight chain or branched alkyl and C$_6$-C$_{10}$ aryl; n and m are each selected independently from 0 to 4 with the proviso that m and n cannot be 0 at the same time, and x is selected from 1 to 5;

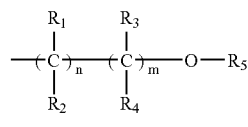

alkoxyalkyls and aryloxyalkyls wherein each of R$_1$-R$_4$ is the same as or different from one another, with each being independently selected from among hydrogen, C$_1$-C$_6$ alkyl, and C$_6$-C$_{10}$ aryl; R$_5$ is selected from among C$_1$-C$_6$ alkyl, and C$_6$-C$_{10}$ aryl; and n and m are selected independently from 0 to 4, with the proviso that m and n cannot be 0 at the same time; each L may be the same as or different from the other, each is a unidentate or multidentate Lewis-base ligand, and each is independently selected from the group consisting of phosphines, tertiary phosphines, ethers, polyethers, amines, alkylamines, polyamines, glymes, crown ethers, crown thioethers, cyclic polyamines (cyclenes), thioglymes, C$_2$-C$_6$ alkynes, azoles, imidazoles, C$_2$-C$_6$ alkenes, pyridines, bipyridines, isonitriles, carbenes and hetero-carbenes;

(ii)

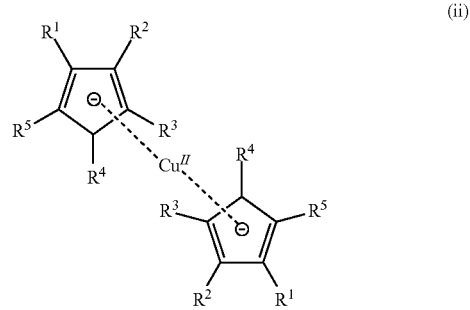

wherein each of R$^1$, R$^2$, R$^3$, R$^4$ and R$^5$ may be the same as or different from the others, and each is independently selected from among hydrogen, C$_1$-C$_6$ alkyl, C$_1$-C$_6$ alkenyl, C$_6$-C$_{10}$ aryl, C$_1$-C$_6$ alkoxy, C$_3$-C$_6$ alkylsilyl, C$_1$-C$_6$ amino, hydrazino of the formula R$_a$R$_b$NNR$_c$— wherein each of R$_a$, R$_b$ and R$_c$ may be the same as or different from one another and each is independently selected from among C$_1$-C$_6$ alkyl, and pendant ligands including functional group(s) providing further coordination to the metal center, selected from the group consisting of aminoalkyl, alkoxyalkyl, aryloxyalkyl, imidoalkyl, and acetylalkyl, and groups of the following formulae:

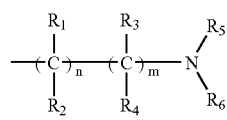

-continued

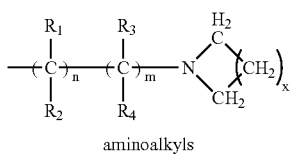
aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

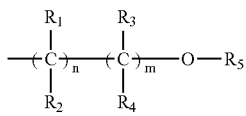
alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time;

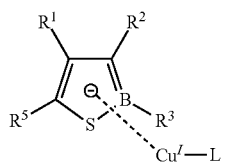

(iii)

wherein each of $R^1$, $R^2$, $R^3$, $R^4$ and $R^5$ may be the same as or different from the others, and each is independently selected from among hydrogen, $C_1$-$C_6$ alkyl, $C_1$-$C_6$ alkenyl, $C_6$-$C_{10}$ aryl, $C_1$-$C_6$ alkoxy, $C_3$-$C_6$ alkylsilyl, $C_1$-$C_6$ amino, hydrazino of the formula $R_aR_bNNR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, selected from the group consisting of aminoalkyl, alkoxyalkyl, aryloxyalkyl, imidoalkyl, and acetylalkyl, and groups of the following formulae:

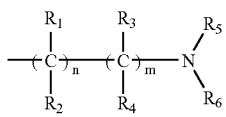

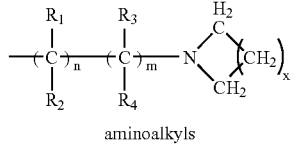
aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

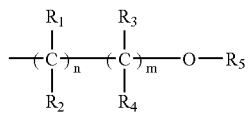
alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time; each L may be the same as or different from the other, each is a unidentate or multidentate Lewis-base ligand, and each is independently selected from the group consisting of phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and hetero-carbenes;

(iv)

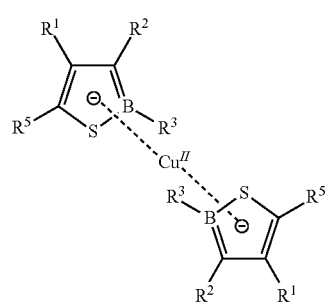

wherein each of $R^1$, $R^2$, $R^3$, $R^4$ and $R^5$ may be the same as or different from the others, and each is independently selected from among hydrogen, $C_1$-$C_6$ alkyl, $C_1$-$C_6$ alkenyl, $C_6$-$C_{10}$ aryl, $C_1$-$C_6$ alkoxy, $C_3$-$C_6$ alkylsilyl, $C_1$-$C_6$ amino, hydrazino of the formula $R_aR_bNNR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, selected from the group consisting of aminoalkyl, alkoxyalkyl, aryloxyalkyl, imidoalkyl, and acetylalkyl, and groups of the following formulae:

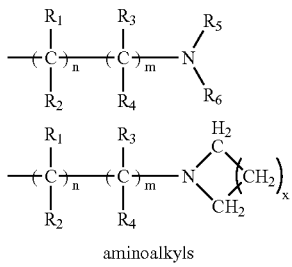

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

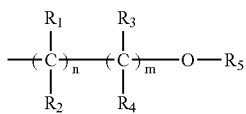

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time;

(v)

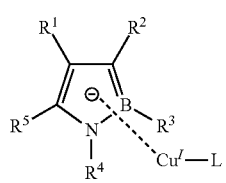

wherein each of $R^1$, $R^2$, $R^3$, $R^4$ and $R^5$ may be the same as or different from the others, and each is independently selected from among hydrogen, $C_1$-$C_6$ alkyl, $C_1$-$C_6$ alkenyl, $C_6$-$C_{10}$ aryl, $C_1$-$C_6$ alkoxy, $C_3$-$C_6$ alkylsilyl, $C_1$-$C_6$ amino, hydrazino of the formula $R_aR_bNNR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, selected from the group consisting of aminoalkyl, alkoxyalkyl, aryloxyalkyl, imidoalkyl, and acetylalkyl, and groups of the following formulae:

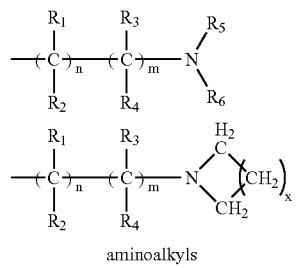

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

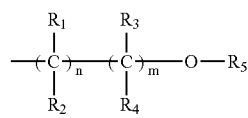

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time; each L may be the same as or different from the other, each is a unidentate or multidentate Lewis-base ligand, and each is independently selected from the group consisting of phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and hetero-carbenes;

(vi)

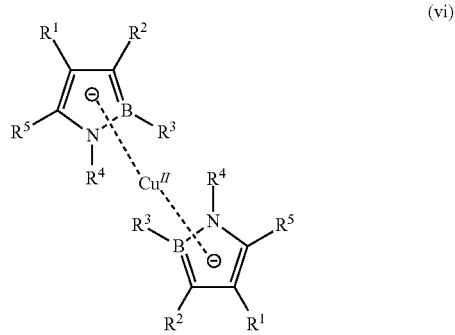

wherein each of $R^1$, $R^2$, $R^3$, $R^4$ and $R^5$ may be the same as or different from the others, and each is independently selected from among hydrogen, $C_1$-$C_6$ alkyl, $C_1$-$C_6$ alkenyl, $C_6$-$C_{10}$ aryl, $C_1$-$C_6$ alkoxy, $C_3$-$C_6$ alkylsilyl, $C_1$-$C_6$ amino, hydrazino of the formula $R_aR_bNNR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, selected from the group consisting of aminoalkyl, alkoxyalkyl, aryloxyalkyl, imidoalkyl, and acetylalkyl, and groups of the following formulae:

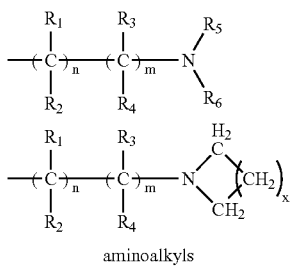

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

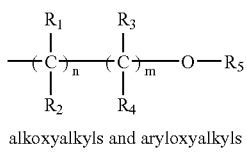

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time;

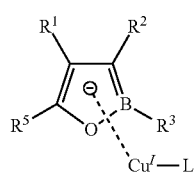

(vii)

wherein each of $R^1$, $R^2$, $R^3$, $R^4$ and $R^5$ may be the same as or different from the others, and each is independently selected from among hydrogen, $C_1$-$C_6$ alkyl, $C_1$-$C_6$ alkenyl, $C_6$-$C_{10}$ aryl, $C_1$-$C_6$ alkoxy, $C_3$-$C_6$ alkylsilyl, $C_1$-$C_6$ amino, hydrazino of the formula $R_aR_bNNR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, selected from the group consisting of aminoalkyl, alkoxyalkyl, aryloxyalkyl, imidoalkyl, and acetylalkyl, and groups of the following formulae:

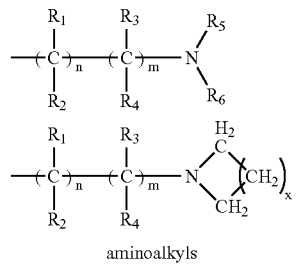

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

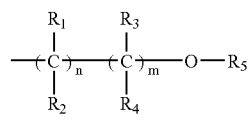

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time; L is a unidentate or multidentate Lewis-base ligand selected from the group consisting of phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and hetero-carbenes;

(viii)

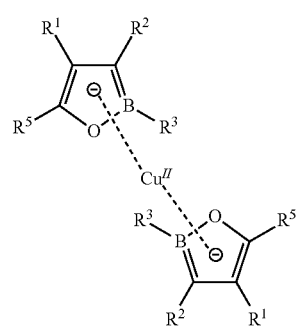

wherein each of $R^1$, $R^2$, $R^3$, $R^4$ and $R^5$ may be the same as or different from the others, and each is independently selected from among hydrogen, $C_1$-$C_6$ alkyl, $C_1$-$C_6$ alkenyl, $C_6$-$C_{10}$ aryl, $C_1$-$C_6$ alkoxy, $C_3$-$C_6$ alkylsilyl, $C_1$-$C_6$ amino, hydrazino of the formula $R_aR_bNNR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, selected from the group consisting of aminoalkyl, alkoxyalkyl, aryloxyalkyl, imidoalkyl, and acetylalkyl, and groups of the following formulae:

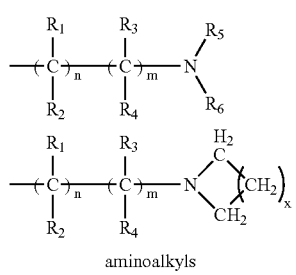

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

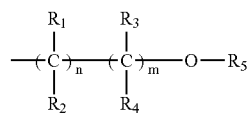

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time;

and a solvent medium.

2. The copper precursor formulation of claim 1, wherein the solvent medium comprises a solvent selected from the group consisting of alkane solvents, hexane, heptane, octane, pentane, aryl solvents, benzene, toluene, amines, triethylamine, tert-butylamine, imines, carbodiimides, N,N'-diisopropylcarbodiimide, alcohols, ethers, ketones, aldehydes, amidines, guanadines, and isoureas.

3. A precursor vapor composition, comprising a vapor of a copper precursor composition of claim 1.

4. A reagent source package, comprising a storage and dispensing vessel containing a copper precursor composition of claim 1.

5. A method of making a cyclopentadienyl-type copper precursor, comprising carrying out a synthesis process comprising a synthetic route selected from the group consisting of:

(I) the synthetic route comprising

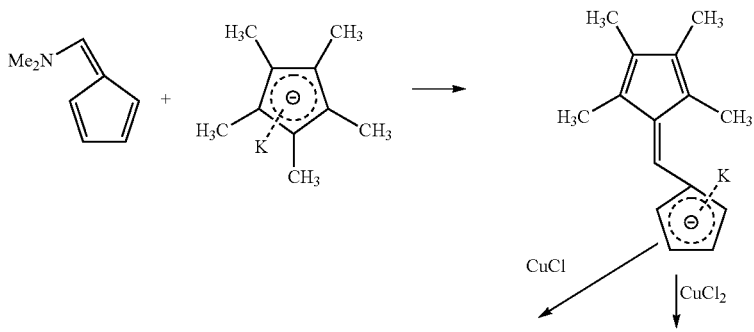

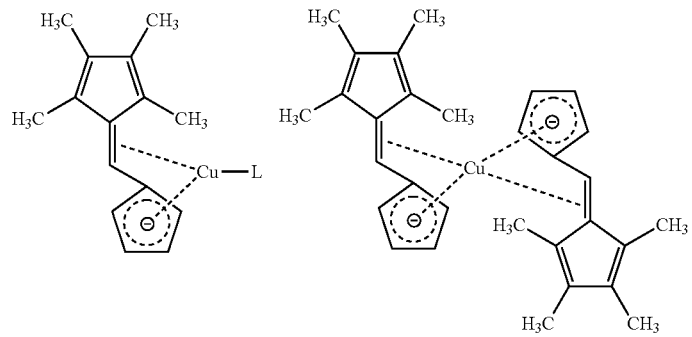

wherein L is a unidentate or multidentate Lewis-base ligand selected from the group consisting of phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and hetero-carbenes; and (II) the synthetic route corresponding to synthetic route (I) wherein cyclopentadienyl substituents instead of being all methyl are each independently selected from among hydrogen, $C_1$-$C_6$ alkyl, $C_1$-$C_6$ alkenyl, $C_6$-$C_{10}$ aryl, $C_1$-$C_6$ alkoxy, $C_3$-$C_6$ alkylsilyl, $C_1$-$C_6$ amino, hydrazino of the formula $R_aR_bNNR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, such as, for example, aminoalkyl, alkoxyalkyl, aryloxyalkyl, imidoalkyl, and acetylalkyl, wherein suitable groups in these classes include those of the following formulae:

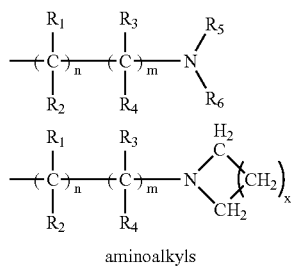

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

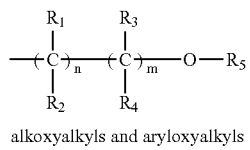

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time; and with L being a unidentate or multidentate Lewis-base ligand selected from the group consisting of phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and hetero-carbenes; and recovering said cyclopentadienyl-type copper precursor from a reaction volume including reactants and products of said synthesis.

6. A copper precursor compound selected from the group consisting of CpCu(CyNC), EtCpCu(tBuNC), and MeCpCu(tBuNC), wherein Cp is cyclopentadienyl, Cy is cyclohexyl, Et is ethyl, and tBu is tertiary butyl.

7. The copper precursor compound of claim 6, comprising CpCu(CyNC).

8. The copper precursor compound of claim 6, comprising EtCpCu(tBuNC).

9. The copper precursor compound of claim 6, comprising MeCpCu(tBuNC).

10. A copper precursor formulation comprising a copper precursor compound of claim 6 and a solvent medium.

11. The copper precursor formulation of claim 10, wherein the solvent medium comprises a solvent selected from the group consisting of alkane solvents, hexane, heptane, octane, pentane, aryl solvents, benzene, toluene, amines, triethylamine, tert-butylamine, imines, carbodiimides, N,N'-diisopropylcarbodiimide, alcohols, ethers, ketones, aldehydes, amidines, guanadines, and isoureas.

12. A precursor vapor composition, comprising a vapor of a copper precursor compound of claim 6.

13. A reagent source package, comprising a storage and dispensing vessel containing a copper precursor compound of claim 6.

14. A copper precursor compound selected from the group consisting of compounds of formulae (i)-(viii):

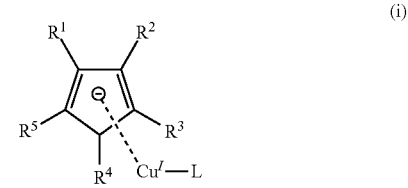

(i)

wherein each of $R^1$, $R^2$, $R^3$, $R^4$ and $R^5$ may be the same as or different from the others, and each is independently selected from among hydrogen, $C_1$-$C_6$ alkyl, $C_1$-$C_6$ alkenyl, $C_6$-$C_{10}$ aryl, $C_1$-$C_6$ alkoxy, $C_3$-$C_6$ alkylsilyl, $C_1$-$C_6$ amino, hydrazino of the formula $R_aR_bNNR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, selected from the group consisting of aminoalkyl, alkoxyalkyl, aryloxyalkyl, imidoalkyl, and acetylalkyl, and groups of the following formulae:

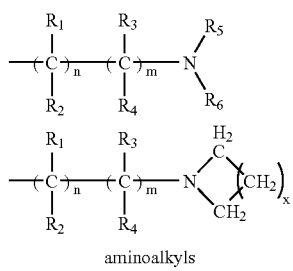

aminoalkyls

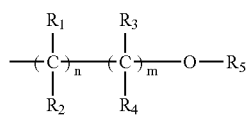

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time; each L may be the same as or different from the other, each is a unidentate or multidentate Lewis-base ligand, and each is independently selected from the group consisting of ethers, polyethers, amines, alkylamines, polyamines, glymes, crown ethers, crown thioethers, cyclic polyamines (cyclenes), thioglymes, $C_2$-$C_6$ alkynes, azoles, imidazoles, pyridines, bipyridines, and isonitriles;

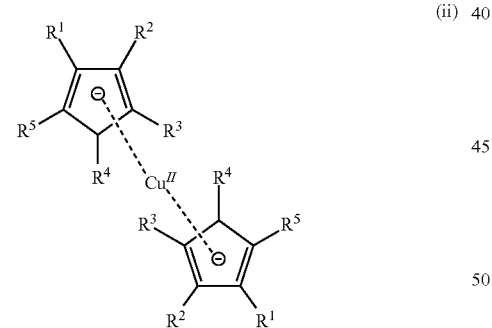
(ii)

wherein each of $R^1$, $R^2$, $R^3$, $R^4$ and $R^5$ may be the same as or different from the others, and each is independently selected from among $C_1$-$C_6$ alkyl, $C_1$-$C_6$ alkenyl, $C_6$-$C_{10}$ aryl, $C_1$-$C_6$ alkoxy, $C_3$-$C_6$ alkylsilyl, $C_1$-$C_6$ amino, hydrazino of the formula $R_aR_bNNR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, selected from the group consisting of aminoalkyl, alkoxyalkyl, aryloxyalkyl, imidoalkyl, and acetylalkyl, and groups of the following formulae:

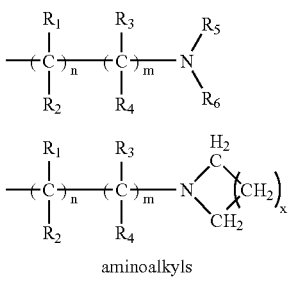

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

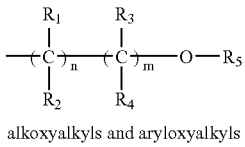

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time;

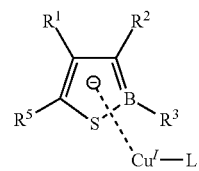
(iii)

wherein each of $R^1$, $R^2$, $R^3$, $R^4$ and $R^5$ may be the same as or different from the others, and each is independently selected from among hydrogen, $C_1$-$C_6$ alkyl, $C_1$-$C_6$ alkenyl, $C_6$-$C_{10}$ aryl, $C_1$-$C_6$ alkoxy, $C_3$-$C_6$ alkylsilyl, $C_1$-$C_6$ amino, hydrazino of the formula $R_aR_bNNR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, selected from the group consisting of aminoalkyl, alkoxyalkyl, aryloxyalkyl, imidoalkyl, and acetylalkyl, and groups of the following formulae:

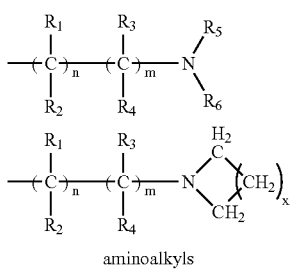

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

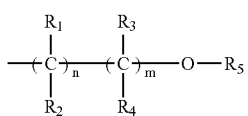

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time; each L may be the same as or different from the other, each is a unidentate or multidentate Lewis-base ligand, and each is independently selected from the group consisting of ethers, polyethers, amines, alkylamines, polyamines, glymes, crown ethers, crown thioethers, cyclic polyamines (cyclenes), thioglymes, $C_2$-$C_6$ alkynes, azoles, imidazoles, pyridines, bipyridines, and isonitriles;

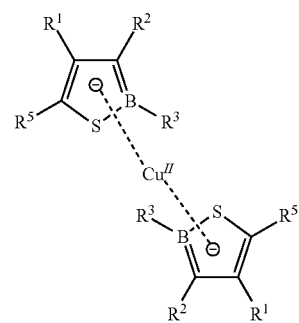

(iv)

wherein each of $R^1$, $R^2$, $R^3$, $R^4$ and $R^5$ may be the same as or different from the others, and each is independently selected from among hydrogen, $C_1$-$C_6$ alkyl, $C_1$-$C_6$ alkenyl, $C_6$-$C_{10}$ aryl, $C_1$-$C_6$ alkoxy, $C_3$-$C_6$ alkylsilyl, $C_1$-$C_6$ amino, hydrazino of the formula $R_aR_bNNR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, selected from the group consisting of aminoalkyl, alkoxyalkyl, aryloxyalkyl, imidoalkyl, and acetylalkyl, and groups of the following formulae:

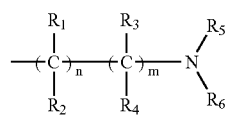

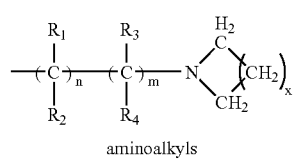

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

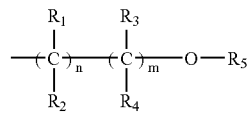

alkoxyalkyls and aryloxyalkyls wherein each of $R_1$-$R_4$ is the same as or, different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time;

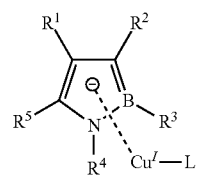

(v)

wherein each of $R^1$, $R^2$, $R^3$, $R^4$ and $R^5$ may be the same as or different from the others, and each is independently selected from among hydrogen, $C_1$-$C_6$ alkyl, $C_1$-$C_6$ alkenyl, $C_6$-$C_{10}$ aryl, $C_1$-$C_6$ alkoxy, $C_3$-$C_6$ alkylsilyl, $C_1$-$C_6$ amino, hydrazino of the formula $R_aR_bNNR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, selected from the group consisting of aminoalkyl, alkoxyalkyl, aryloxyalkyl, imidoalkyl, and acetylalkyl, and groups of the following formulae:

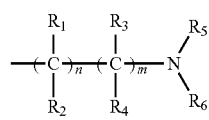

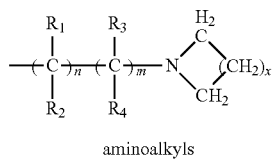

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

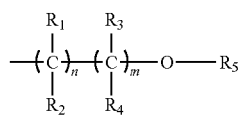

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time; each L may be the same as or different from the other, each is a unidentate or multidentate Lewis-base ligand, and each is independently selected from the group consisting of phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and hetero-carbenes;

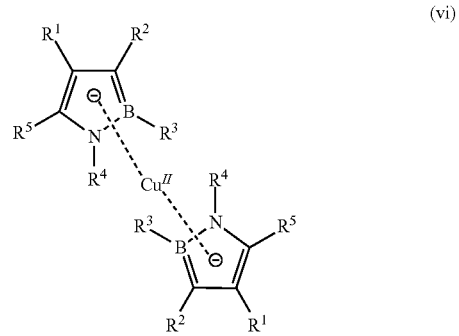

(vi)

wherein each of $R^1$, $R^2$, $R^3$, $R^4$ and $R^5$ may be the same as or different from the others, and each is independently selected from among hydrogen, $C_1$-$C_6$ alkyl, $C_1$-$C_6$ alkenyl, $C_6$-$C_{10}$ aryl, $C_1$-$C_6$ alkoxy, $C_3$-$C_6$ alkylsilyl, $C_1$-$C_6$ amino, hydrazino of the formula $R_aR_bNNR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, selected from the group consisting of aminoalkyl, alkoxyalkyl, aryloxyalkyl, imidoalkyl, and acetylalkyl, and groups of the following formulae:

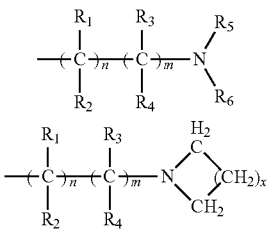

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

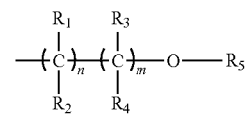

alkoxyalkyls and aryloxyalkyls wherein each of $R_1$-$R_4$ is the same as or different from one another, with each being independently selected from among $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time;

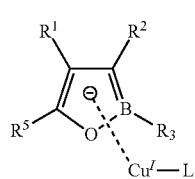

(vii)

wherein each of $R^1$, $R^2$, $R^3$, $R^4$ and $R^5$ may be the same as or different from the others, and each is independently selected from among hydrogen, $C_1$-$C_6$ alkyl, $C_1$-$C_6$ alkenyl, $C_6$-$C_{10}$ aryl, $C_1$-$C_6$ alkoxy, $C_3$-$C_6$ alkylsilyl, $C_1$-$C_6$ amino, hydrazino of the formula $R_aR_bNNR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, selected from the group consisting of aminoalkyl, alkoxyalkyl, aryloxyalkyl, imidoalkyl, and acetylalkyl, and groups of the following formulae:

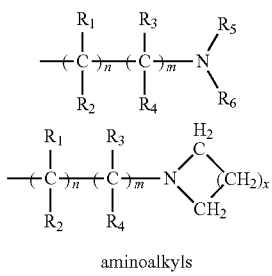

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

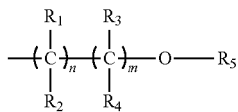

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time; L is a unidentate or multidentate Lewis-base ligand selected from the group consisting of phosphines, tertiary phosphines, ethers, polyethers, amines, alkylamines, polyamines, glymes, crown ethers, crown thioethers, cyclic polyamines (cyclenes), thioglymes, $C_2$-$C_6$ alkynes, azoles, imidazoles, $C_2$-$C_6$ alkenes, pyridines, bipyridines, isonitriles, carbenes and hetero-carbenes; and

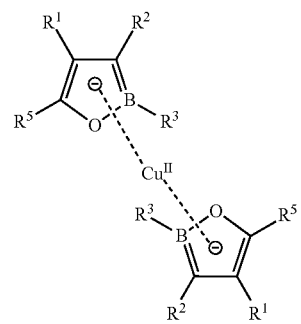

(viii)

wherein each of $R^1$, $R^2$, $R^3$, $R^4$ and $R^5$ may be the same as or different from the others, and each is independently selected from among hydrogen, $C_1$-$C_6$ alkyl, $C_1$-$C_6$ alkenyl, $C_6$-$C_{10}$ aryl, $C_1$-$C_6$ alkoxy, $C_3$-$C_6$ alkylsilyl, $C_1$-$C_6$ amino, hydrazino of the formula $R_aR_bNNR_c$— wherein each of $R_a$, $R_b$ and $R_c$ may be the same as or different from one another and each is independently selected from among $C_1$-$C_6$ alkyl, and pendant ligands including functional group(s) providing further coordination to the metal center, selected from the group consisting of aminoalkyl, alkoxyalkyl, aryloxyalkyl, imidoalkyl, and acetylalkyl, and groups of the following formulae:

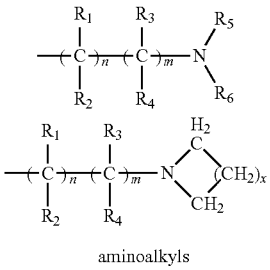

aminoalkyls wherein each of $R_1$-$R_4$ is the same as or different from one another, with each being independently selected from among hydrogen and $C_1$-$C_6$ straight chain or branched alkyl, $C_1$-$C_6$ straight chain or branched alkoxy, $C_6$-$C_{10}$ aryl and $NR_5R_6$; each of $R_5$ and $R_6$ is the same as or different from the other, with each being independently selected from among $C_1$-$C_6$ straight chain or branched alkyl and $C_6$-$C_{10}$ aryl; n and m are each selected independently from 0 to 4 with the proviso that m and n cannot be 0 at the same time, and x is selected from 1 to 5;

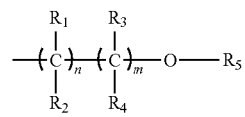

alkoxyalkyls and aryloxyalkyls wherein each of $R_1$-$R_4$ is the same as or different from one another, with each being independently selected from among hydrogen, $C_1$-$C_6$ alkyl, and $C_6$-$C_{10}$ aryl; $R_5$ is selected from among $C_1$-$C_6$ alkyl, and $C_6$-$C_{10}$ aryl; and n and m are selected independently from 0 to 4, with the proviso that m and n cannot be 0 at the same time.

\* \* \* \* \*

UNITED STATES PATENT AND TRADEMARK OFFICE
CERTIFICATE OF CORRECTION

PATENT NO. : 7,964,746 B2
APPLICATION NO. : 12/058751
DATED : June 21, 2011
INVENTOR(S) : Tianniu Chen It is certified that error appears in the above-identified patent and that said Letters Patent is hereby corrected as shown below:

Column 15, line 38: "$Na(C_2(R^1R^2R^3R^4R^5) + NaB_3H_2$" should be -- $Na(C_5(R^1R^2R^3R^4R^5)) + NaB_3H_8$ --.

Column 15, line 38: "$Na(C_3(R^1R^2R^3R^4R^5)$" should be -- $Na(C_5(R^1R^2R^3R^4R^5))$ --.

Column 20, line 50: "$Na(C_2(R^1R^2R^3R^4R^5)$" should be -- $Na(C_5(R^1R^2R^3R^4R^5))$ --.

Column 39, line 40: "$R_a$, $R_b$ and $R_a$" should be -- $R_a$, $R_b$ and $R_c$ --.

Signed and Sealed this
Thirteenth Day of September, 2011

David J. Kappos
*Director of the United States Patent and Trademark Office*